United States Patent
Lyte et al.

(10) Patent No.: US 12,152,270 B2
(45) Date of Patent: Nov. 26, 2024

(54) NEUROTRANSMITTER TRANSPORT IN PROBIOTICS

(71) Applicants: Iowa State University Research Foundation, Inc., Ames, IA (US); REGENTS OF THE UNIVERSITY OF MINNESOTA, Minneapolis, MN (US)

(72) Inventors: Mark Lyte, Ames, IA (US); David Robert Brown, Saint Paul, MN (US)

(73) Assignees: Iowa State University Research Foundation, Inc., Ames, IA (US); REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 904 days.

(21) Appl. No.: 17/248,641

(22) Filed: Feb. 1, 2021

(65) Prior Publication Data

US 2021/0155968 A1    May 27, 2021

Related U.S. Application Data

(62) Division of application No. 16/009,629, filed on Jun. 15, 2018, now Pat. No. 10,941,433.

(60) Provisional application No. 62/519,937, filed on Jun. 15, 2017.

(51) Int. Cl.
| | |
|---|---|
| C12Q 1/02 | (2006.01) |
| A61K 31/135 | (2006.01) |
| A61K 31/138 | (2006.01) |
| A61K 31/381 | (2006.01) |
| A61K 31/47 | (2006.01) |
| A61K 31/4709 | (2006.01) |
| A61K 35/747 | (2015.01) |
| C12Q 1/04 | (2006.01) |

(52) U.S. Cl.
CPC ............ *C12Q 1/025* (2013.01); *A61K 31/135* (2013.01); *A61K 31/138* (2013.01); *A61K 31/381* (2013.01); *A61K 31/4709* (2013.01); *A61K 35/747* (2013.01); *C12Q 1/04* (2013.01); *G01N 2500/10* (2013.01); *G01N 2800/304* (2013.01); *G01N 2800/52* (2013.01)

(58) Field of Classification Search
None
See application file for complete search history.

(56) References Cited

U.S. PATENT DOCUMENTS

| | | |
|---|---|---|
| 5,589,168 A | 12/1996 | Allen et al. |
| 6,203,797 B1 | 3/2001 | Perry |
| 6,835,376 B1 | 12/2004 | Neeser et al. |
| 2014/0301995 A1 | 10/2014 | Mayra-Makinen et al. |
| 2016/0058808 A1 | 3/2016 | Hsiao et al. |
| 2016/0129057 A1 | 5/2016 | Jeon et al. |

OTHER PUBLICATIONS

Rieder, Ryan et al., "Microbes and Mental Health: A Review", Brain, Behavior, and Immunity, 66, pp. 9-17. Jan. 24, 2017.
Rogers, Mary A. M. et al., "Depression, Antidepressant Medications, and Risk of Clostridium Difficile Infection", BMC Medicine, 11, pp. 1-11. 2013.
Rudnick, Gary, "What Is An Antidepressant Binding Site Doing in a Bacterial Transporter?", ACS Chemical Biology, vol. 2, No. 9, pp. 606-609. Sep. 21, 2007.
Singh, Satinder K. et al., "Antidepressant Binding Site in a Bacterial Homologue of Neurotransmitter Transporters", Nature Publishing Group, vol. 448, pp. 952-956. Aug. 2007.
Vardy, Eyal et al., "Characterization of Bacterial Drug Antiporters Homologous to Mammalian Neurotransmitter Transporters", Journal of Bacteriology, vol. 187, No. 21, pp. 7518-7525. Nov. 2005.
Wei, Peng et al., "Structural Differences Between Paroxetine and Femoxetine Responsible for Differential Inhibition of *Staphylococcus aureus* Efflux Pumps", Bioorganic & Medicinal Chemistry Letters, 14, pp. 3093-3097. Apr. 10, 2004.
Yaffe, Dana et al., "Functionally Important Carboxyls in a Bacterial Homologue of the Vesicular Monoamine Transporter (VMAT)*", The Journal of Biological Chemistry, vol. 289, No. 49, pp. 34229-34240. Dec. 5, 2014.
Bohnert, Jürgen A., "Efflux Inhibition by Selective Serotonin Reuptake Inhibitors in *Escherichia coli*", Journal of Antimicrobial Chemotherapy, 66, pp. 2057-2060. Jun. 23, 2011.
Dinan, Timothy G et al., "The Microbiome-Gut-Brain Axis in Health and Disease", Crossmark, pp. 77-89. 2016.
Imhann, Floris et al., "The Influence of Proton Pump Inhibitors and Other Commonly Used Medication on the Gut Microbiota", Gut Microbes, pp. 351-358. Jan. 13, 2017.
Kaatz, Glenn W. et al., "Phenylpiperidine Selective Serotonin Reuptake Inhibitors Interfere with Multidrug Efflux Pump Activity in *Staphylococcus aureus*", International Journal of Antimicrobial Agents, 22, pp. 254-261. 2003.
Kantak, Pranish A. et al., "Obsessive-Compulsive-Like Behaviors in House Mice are Attenuated by a Probiotic (*Lactobacillus rhamnosus* GG)", Behavioural Pharmacology, vol. 25, No. 1, pp. 71-79. Oct. 18, 2013.
Kristiansen, J.E. et al., "Non-Antibiotics Reverse Resistance of Bacteria to Antibiotics", in vivo, 24, pp. 751-754. 2010.
Laudy, Agnieszka E. et al., "The Impact of Efflux Pump Inhibitors on the Activity of Selected Non-Antibiotic Medicinal Products Against Gram-Negative Bacteria", Molecules, 22, pp. 1-12. 2017.
Lyte, Mark et al., "Evidence of PMAT- and OCT-like Biogenic Amine Transporters in a Probiotic Strain of Lactobacillus: Implications for Interkingdom Communication within the Microbiota-gut-brain Axis", Plos One, pp. 1-13. Dec. 27, 2017.

(Continued)

*Primary Examiner* — Oluwatosin A Ogunbiyi
(74) *Attorney, Agent, or Firm* — McKee, Voorhees & Sease, PLC

(57) ABSTRACT

The present invention is directed to methods of probiotic selection and use based on the capability of microbial biogenic amine uptake as a method for targeted clinical and veterinary applications, including promoting health and well-being and/or treating therapeutic conditions. The present invention utilizes a microbially-focused approach for the development of drug selection and/or probiotic administration in a variety of diseases and disorders.

10 Claims, 16 Drawing Sheets

(56) References Cited

OTHER PUBLICATIONS

Lyte, Mark, "Probiotics Function Mechanistically as Delivery Vehicles for Neuroactive Compounds: Microbial Endocrinology in The Design and Use of Probiotics", Bioessays, 33, pp. 574-581. 2011.

Macedo, Danielle et al., "Antidepressants, Antimicrobials or Both? Gut Microbiota Dysbiosis in Depression and Possible Implications of the Antimicrobial Effects of Antidepressant Drugs for Antidepressant Effectiveness", Journal of Affective Disorders, 208, pp. 22-32. Sep. 18, 2016.

Molnár, J. et al., "The Plasmid Curing Action of Imipramine in *Escherichia coli* K12", Genet. Research Camb., 31, pp. 197-201. May 10, 1977.

Munoz-Bellido, J. L. et al., "Antimicrobial Activity of Psychotropic Drugs Selective Serotonin Reuptake Inhibitors", International Journal of Antimicrobial Agents, 14, pp. 177-180. 2000.

Lyte, Mark et al., "Microbial Endocrinology", Springer, pp. 1-323. 2010.

Androutsellisl-Theotokist, Andreas et al., "Characterization of a Functional Bacterial Homologue of Sodium-dependent Neurotransmitter Transporters", The Journal of Biological Chemistry, vol. 278, No. 15, pp. 12703-12709. Feb. 4, 2003.

Lass-florla$^{a*}$, C. et al., "Antifungal Properties of Selective Serotonin Reuptake Inhibitors Against Aspergillus Species in vitro", Journal of Antimicrobial Chemotherapy, 48, pp. 775-779. 2001.

Kline, Mark D. et al., "Acidophilus for Sertraline-Induced Diarrhea", Letters to the Editor, Am J. Psychiatry, pp. 1521-1522. Oct. 1994.

Piddock, Laura J. V., et al., "Natural and Synthetic Compounds Such as Trimethoprim Behave As Inhibitors of Efflux in Gram-Negative Bacteria", Journal of Antimicrobial Chemotherapy, vol. 65, pp. 1215-1223. Mar. 19, 2010.

Asano Y, et al. "Critical role of gut microbiota in the production of biologically active, free catecholamines in the gut lumen of mice", Am J Physiol Gastrointest Liver Physiol. 2012.

Mawe GM et al., "Serotonin signalling in the gut—functions, dysfunctions and therapeutic targets", Nat Rev Gastroenterol Hepatol, 10(8): pp. 473-486. 2013.

Yang, Y-X et al., "Determination of biogenic amines in digesta by high performance liquid chromatography with precolumn dansylation", Anal Lett. 2015.

Lyte, M et al., "Stress at the Intestinal Surface: Catecholamines and Mucosa-Bacteria Interactions", Cell Tissue Research, 343(1) pp. 23-32. 2011.

Sandrini S et al., "Microbial Endocrinology: Host-Bacteria Communication Within the Gut Microbiome", J Endocrinol. 2015.

Moreira CG, et al. "The Epinephrine/Norepinephrine/Autoinducer-3 Interkingdom Signaling System in *Escherichia coli* O157:H7", Adv Exp Med Biology, pp. 247-261. 2016.

Lyte, M, et al. "Stimulation of *Staphylococcus* Epidermidis Growth and Biofilm Formation by Catecholamine Inotropes", Lancet. 2003.

Lyte, M. "The Biogenic Amine Tyramine Modulates the Adherence of *Escherichia coli* O157:H7 to Intestinal Mucosa" J Food Prot., 67(5) pp. 878-883. 2004.

Pessione E, "Cirrincione S. Bioactive Molecules Released in Food by Lactic Acid Bacteria: Encrypted Peptides and Biogenic Amines. Frontiers in Microbiology" 2016.

Yano JM, et al. "Indigenous Bacteria from the Gut Microbiota Regulate Host Serotonin Biosynthesis", Cell, 161(2) pp. 264-276. 2015.

Lin L, et al., "SLC Transporters as Therapeutic Targets: Emerging Opportunities", Nat Rev Drug Discovery, 14(8) pp. 543-560. 2015.

Yamahita, A et al., "Crystal Structure of a Bacterial Homologue of Na+/Cl—Dependent Neurotransmitter Transporters", Nature. 437(7056) pp. 215-223. 2005.

Lyte, M., "Probiotics Function Mechanistically as Delivery Vehicles for Neuroactive Compounds: Microbial Endocrinology in the Design and Use of Probiotics", Bioessays, vol. 33, pp. 574-581. 2011.

Beikmann Brenda, S et al., "Serotonin Uptake is Largely Mediated by Platelets Versus Lymphocytes in Peripheral Blood Cells", ACS Chem Neuroscience, vol. 4, pp. 161-170. 2013.

Salas-Jara MJ et al., "Biofilm Forming Lactobacillus: New Challenges for the Development of Probiotics", Microorganisms, vol. 4, No. 35, pp. 1-14. 2016.

Jorgensen S et al., "Validation of a Fluorescence-Based High-Throughput Assay for the Measurement of Neurotransmitter Transporter Uptake Activity", Journal of Neuroscience Methods, vol. 169, pp. 168-176. Dec. 7, 2007.

Duan H, et al., "Potent and Selective Inhibition of Plasma Membrane Monoamine Transporter by HIV Protease Inhibitors", Drug Metab Dispos, vol. 43, pp. 1773-1780. Nov. 2015.

Wang, J. "The Plasma Membrane Monoamine Transporter (PMAT): Structure, Function, and Role in Organic Cation Disposition", Clinical Pharmacology Therapeutics, vol. 100, No. 5, pp. 489-499. Aug. 10, 2016.

Wagner, DJ, et al., "Polyspecific Organic Cation Transporters and Their Impact on Drug Intracellular Levels and Pharmacodynamics", Pharmacological Research, vol. 111, pp. 237-246. Jun. 16, 2016.

Schömig E, et al., "1,1'-diethyl-2,2'-cyanine (decynium22) Potently Inhibits the Renal Transport of Organic Cations", Archives of Pharmacology, vol. 347, pp. 379-383. Jan. 19, 1993.

Yarbrough, JM et al., "Bacterial Inhibitory Effects of Nitrite: Inhibition of Active Transport, but not of Group Translocation, and of Intracellular Enzymes", Applied and Environmental Microbiology, vol. 39, No. 4, pp. 831-834. Apr. 1980.

Salomon JJ, et al., "Transport of the Fluorescent Organic Cation 4-(4-(dimethylamino)styryl)-N-methylpyridinium Iodide (ASP+) in Human Respiratory Epithelial Cells", European Journal of Pharmaceutics and Biopharmaceutics, vol. 81, pp. 351-359. 2012.

Yang, Qian et al., "Norepinephrine and Dopamine Increase Motility, Biofilm Formation, and Virulence of Vibrio Harveyi", Frontiers in Microbiology, vol. 5, Article 584, pp. 1-12. Nov. 6, 2014.

Bravo, Javier A. et al., "Ingestion of Lactobacillus Strain Regulates Emotional Behavior and Central GABA Receptor Expression in a Mouse Via the Vagus Nerve", PNAS, vol. 108, No. 38, pp. 16050-16055. Sep. 20, 2011.

Forsyth, Christopher B. et al., "Lactobacillus GG Treatment Ameliorates Alcohol-Induced Intestinal Oxidative Stress, Gut Leakiness, and Liver Injury in a Rat Model of Alcoholic Steatohepatitis", Alcohol, vol. 43, pp. 163-172. Dec. 31, 2008.

Freestone, Primrose PE et al., "Blockade of Catecholamine-induced Growth by Adrenergic and Dopaminergic Receptor Antagonists in *Escherichia coli* O157:H7, *Salmonella enterica* and *Yersinia Enterocolitica*", BMC Microbiology, pp. 1-13. Jan. 30, 2007.

Grover, Madhusudan et al., "Effects on Gastrointestinal Functions and Symptoms of Serotonergic Psychoactive Agents Used in Functional Gastrointestinal Diseases", J Gastroenterol, vol. 48, pp. 177-181. 2013.

Höglund, Pär J., et al., "The Solute Carrier Families Have a Remarkably Long Evolutionary History with the Majority of the Human Families Present Before Divergence of Bilaterian Species", Mol. Biol. Evol., vol. 28, pp. 1531-1541. Dec. 24, 2010.

Koldsø et al., "Insights to Ligand Binding to the Monoamine Transporters-from Homology Modeling to LeuBAT and dDAT", Frontiers in Pharmacology, vol. 6, Article 208, pp. 1-8. Sep. 24, 2015.

Lambert, R.J.W. et al., "A Study of the Minimum Inhibitory Concentration and Mode of Action of Oregano Essential Oil, Thymol and Carvacrol", Journal of Applied Microbiology, vol. 91, pp. 453-462. Apr. 4, 2001.

Lyte, Mark et al., "Alpha and Beta Adrenergic Receptor Involvement in Catecholamine-Induced Growth of Gram-Negative Bacteria", Biochemical and Biophysical Research Communications, vol. 190, No. 2, pp. 447-452. Jan. 29, 1993.

Lyte, Mark, "Microbial Endocrinology in the Pathogenesis of Infectious Disease", Microbiology Spectrum, pp. 1-24. Mar. 25, 2016.

Lyte, Mark, "Microbial Endocrinology", Gut Microbes, vol. 5, No. 3, pp. 381-389. 2014.

Lyte, Mark et al., "Microbial Endocrinology: The Microbiota-Gut-Brain Axis in Health and Disease", Advances in Experimental Medicine and Biology, vol. 817, pp. 1-42. 2014.

NEUROTRANSMITTER TRANSPORT IN PROBIOTICS

CROSS REFERENCE TO RELATED APPLICATION

This application is a Divisional Application of U.S. Ser. No. 16/009,629, now U.S. Pat. No. 10,941,433, filed on Jun. 15, 2018, which claims priority under claims priority under 35 U.S.C. § 119 to provisional application Ser. No. 62/519,937, filed Jun. 15, 2017, all of which are herein incorporated by reference in their entirety.

GRANT REFERENCE

This invention was made with government support under the U.S. Office of Naval Research, contract Grant No. N00014-15-1-2706. The Government has certain rights in this invention.

FIELD OF THE INVENTION

The present invention is directed to methods of identifying and selecting probiotic microbes and compounds based on the expression of neurochemical transporters of probiotic microbes as a method for targeted clinical and veterinary applications, for example, in promoting health and well-being and/or treating therapeutic conditions. Embodiments of the present invention utilizes a microbially-focused pharmacogenomic approach to the identification and selection of probiotic microbes expressing biogenic amine transporters and the selection of compounds which may or may not interact with the transporters in a variety of diseases and disorders.

BACKGROUND OF THE INVENTION

Probiotics are designated as living microorganisms, e.g. bacteria and fungi that may be used for both maintenance of health as well as treatment of specific clinical conditions ranging from oral, gastrointestinal or vaginal infections to the treatment of neuropsychiatric-related behavioral issues. Probiotics are also extensively used in the farm production industry (e.g., fish, fowl, pigs, cattle) as well as in the treatment of companion animals (e.g., reptiles, birds, pocket pets, dogs, cats, horses). A critical impediment to the more widespread use of probiotics in medicine is the lack of understanding of the mechanism(s) by which they may exert their benefits. If the mechanisms are unknown, then becomes nearly impossible to screen the large libraries of probiotics that exist to identify those strains which may be of benefit. The discovery described herein has found a screening approach based upon the microbial endocrinology concept which the inventor has pioneered in the scientific literature.

The concept of microbial endocrinology is based on the ability of a microorganism, such as those designated as "probiotic", to produce and recognize the very same neurochemicals that animals or humans produce. Such recognition and production of neurochemicals would mean that a probiotic can interact with the animal's physiology or behavior and thereby influence host health and disease pathogenesis, which can often involve these substances. Thus, identification of probiotic's capacity to recognize a specific neurochemical becomes the first step of a screening process. In such a case, a neurotransmitter transporter uptake assay is used in conjunction with mammalian cells. In this assay, the ability of the drug to influence the uptake of a known neurochemical that influences behavior, for example dopamine or serotonin, is examined. If the drug can block the uptake, it permits these substances to accumulate in the extracellular fluids bathing target cells and thus has the potential to be an indirectly-acting dopamine or serotonin receptor agonist. The clinically-relevant effects of common medications such as some antidepressant drugs stem from the ability of these drugs to block the re-uptake of biogenic amine into nerve cells, thereby increasing the concentrations of these substances in the extracellular fluid and ultimately producing a positive change in behavior or "happiness" of a person.

Previous work in the field of microbe-host interactions has shown that antidepressant drugs can block antimicrobial drug efflux from bacterial cells and can help to surmount antibiotic resistance. Some antidepressants also appear to inhibit plasmid activity of bacteria which prevents some pathogens from growing. Previous work in the field has also shown that gut microorganisms may influence brain and spinal cord function through the production of serotonin or act through a humoral route. It has also been shown that under stressful conditions or intestinal dysbiosis, gut permeability increases and allows for bacterial translocation or a change in the composition of the healthy gut microbial community. These effects in turn could cause a local or systemic inflammatory response, which can influence brain biochemistry.

Recent work by the inventors has revealed, in the context of probiotics, a completely different mechanism though which certain "probiotic" bacteria and possibly other microorganisms can interact with their animal host. The inventors have shown for the first time that certain probiotic strains of bacteria are capable of monoamine transport, which could mediate the uptake of biogenic amines and that are sensitive to drugs that are used worldwide for the control of anxiety, depression, and other mood-related disorders. Identification of the capability of such transportation elucidates a new method by which to utilize known drugs (both clinical and veterinary), as well as design a whole new class of drugs, by which to influence health and brain function.

Neurochemical Transporters

The plasma membrane monoamine transporter (PMAT) and organic cation transporters (OCTs) are typically characterized as low affinity, high capacity systems for the uptake and transport of biogenic monoamines, such as serotonin, norepinephrine, and dopamine, that are involved in a wide array of physiological and neurological processes. The actions of released monoamine neurotransmitters are terminated by these plasma membrane influx transporters that actively remove the neurotransmitters from the extracellular space. In mammalian systems, two distinct influx systems, named uptake1 and uptake2, are responsible for the extracellular clearance of bioactive monoamines. The uptake2 was originally characterized as a $Na^+$- and $Cl^-$-independent, low-affinity, high-capacity transport system in peripheral tissues such as heart and smooth muscle cells. Historically, uptake2 has been associated with monoamine metabolism and was proposed to play a secondary role in monoamine uptake. However, emerging data suggest that these transporters may be actively involved in various monoamine signaling pathways and may represent promising targets for neuropsychiatric and neurodegenerative disorders.

Organic cation transporters (OCT; e.g., OCT1, OCT2, and OCT3) and the plasma membrane monoamine transporter (PMAT) are the two most prominent uptake2 transport systems for endogenous monoamines. PMAT and OCT both transport a broad range of organic cations, including monoamine neurotransmitters and the prototypical organic cations 1-methyl-4-phenylpyridinium (MPP+) and tetraethylammonium (TEA). OCT3- and PMAT-mediated monoamine transport show classic uptake2 characteristics, such as Na+ and Cl− independency and low substrate affinity but high transport capacity. Both transporters are highly sensitive to inhibition by the isocyanine compound, decynium 22 (D22). To date, no known reports have indicated the expression of monoamine transport systems in bacteria that are analogous to the well-characterized mammalian transporters and display sensitivity to antidepressant drugs that have been classified as reuptake inhibitors in animal cells.

Accordingly, it is an objective of the claimed invention to develop a method to select probiotics for targeted clinical and veterinary applications.

A further object of the invention is a method of mitigating adverse effects of antidepressant and other substrates for these uptake transporters relating to excessive extracellular biogenic amine concentrations in the gut or other hollow organs of a subject in need thereof.

A further object of the invention is a method of specifically manipulating the abundance of a member of a microbial community in a host subject based on its capability to uptake monoamines.

A further object of the invention is a method of identifying compounds which do not interact with members of a microbial community within a host based on the capability to intake monoamines.

One aspect, feature or advantage of the present invention provides a diagnostic test and/or method of screening a subject to optimize clinical therapies in the treatment of a variety of disorders, for example, depression.

Other objects, advantages and features of the present invention will become apparent from the following specification taken in conjunction with the accompanying figures.

BRIEF SUMMARY OF THE INVENTION

An advantage of the invention is the ability to determine which probiotic strains of a microbe will work to benefit human or animal health, especially in the context of associated conditions such as stress. It is an advantage of the present invention that probiotic bacteria, such as those belonging to the genus Lactobacilli, possessing OCT- as well as PMAT-like systems for the uptake and transport of biogenic amines and related-drugs that have been utilized to influence host physiology and brain function in veterinary or human clinical practice.

In an embodiment, the present invention provides a method for selecting or identifying probiotic strains capable of uptake and/or transport of biogenic amines and/or related substrates, comprising the steps of: screening for the presence of at least one transporter capable of uptake of biogenic amines; and selecting at least one bacterial strain which expresses at least one transporter capable of binding or transporting the biogenic amine and/or related substrate.

In one aspect of the invention, the step of screening comprises: contacting the probiotic strain with a fluorophore, such as IDT307 (4-[p-(Dimethylamino)phenyl]-1-methylpyridinium iodide) or ASP+ ([4-(4-(diethylamino) styryl)-N-methylpyridinium iodide]), for a sufficient amount of time; and detecting the ability of said fluorophore to enter said strain as determined by increased fluorescence when compared to a probiotic strain which does not express a transporter capable of binding the biogenic amine and/or related substrate.

In an embodiment, the present invention provides a method of reducing the concentrations of free biogenic amines and/or related substrates in the luminal fluids of the gut or other hollow organ of a subject in need thereof, comprising: administering to the subject an effective amount of at least one probiotic strain expressing a transporter capable of binding to said biogenic amines and/or related substrates in the gastrointestinal tract, gut, or other hollow organ (e.g. vagina) of the subject. Wherein the "gut" includes the gastrointestinal tract as well as organs served by the blood supply to and from the gut.

In another embodiment, the invention provides a method of specifically manipulating the abundance of a member of a microbial community of a host to a target, the method comprising (a) obtaining a sample comprising a representative population of a microbial community from a subject; (b) screening the microbial community for the presence or absence of strains expressing a plasma membrane monoamine transporter (PMAT)- and/or one or more organic cation transporter (OCT)-like activity(ies); (c) determining the target transporter uptake capability profile for said subject; and (d) administering to said subject an effective amount of a probiotic strain thereby providing the target uptake capability profile in the said subject.

In another embodiment, the invention provides a method of screening for compounds which do not influence a microbial community of a host, the method comprising (a) obtaining a sample comprising a representative population of a microbial community from a subject; (b) screening the microbial community for the presence or absence of strains capable of uptaking at least one biogenic amine; (c) administering to said microbial community an effective amount of compounds; and (d) screening the compounds which do not interact with the microbial community. Screening may be done by methods well known in the art such as, but not limited to, detecting a lack of attenuation of a fluorophore recapture of the compound from the media, detecting a radioisotope in either the media or inside the microbes, or using various microscopy techniques to identify a labeled compound. When transport proteins underlying these functionalities are characterized, their detection by specific binding of a labeled ligand (substrate) could also be employed While multiple embodiments are disclosed, still other embodiments of the present invention will become apparent to those skilled in the art from the following detailed description, which shows and describes illustrative embodiments of the invention. Accordingly, the figures and detailed description are to be regarded as illustrative in nature and not restrictive.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

Figure 1:
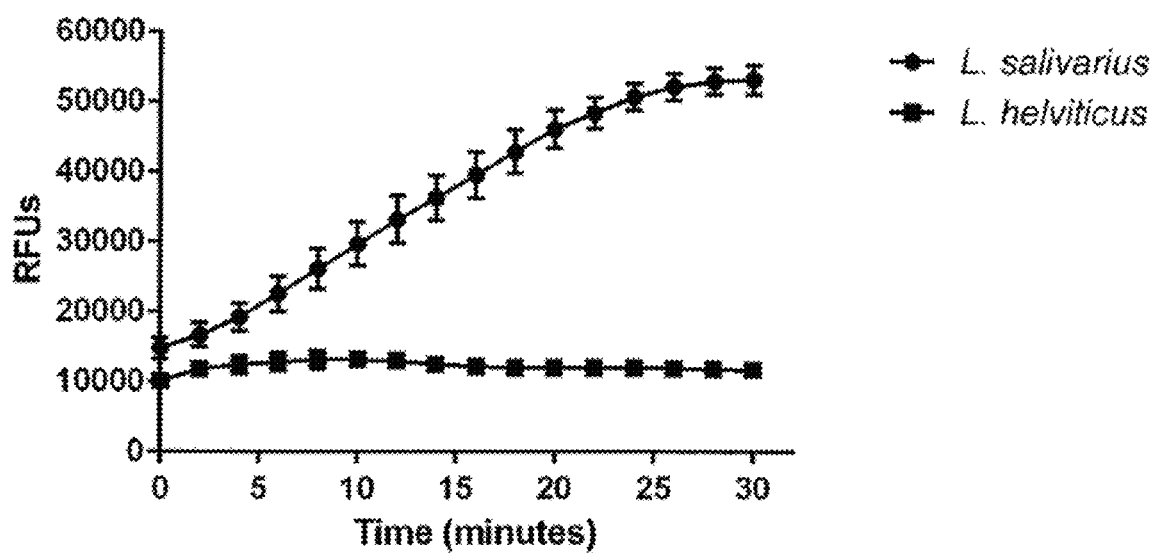
FIG. 1 shows the identification of PMAT-like transport in *L. salivarius*

Reference to various embodiments does not limit the scope of the invention. Figures represented herein are not limitations to the various embodiments according to the invention and are presented for exemplary illustration of the invention.

DETAILED DESCRIPTION OF THE INVENTION

The present invention relates to methods of detecting and selecting compounds and/or probiotic strains for optimal administration of drugs and/or probiotic strains to subjects as it relates to neurochemical transporters expressed by said probiotic strains or members of the host's microbial community. The present methods have many advantages over conventional administration of probiotics and/or biogenic amine-based drugs and other substrates. For example, a significant gap in knowledge on the use of probiotics in medicine is the lack of understanding of the mechanism(s) by which they may exert their benefits. Embodiments of the present invention have found a detecting approach based upon microbial endocrinology, which can be utilized to promote health and well-being in various human and veterinary applications.

The embodiments of this invention are not limited to particular methods, which can vary and are understood by skilled artisans. It is further to be understood that all terminology used herein is for the purpose of describing particular embodiments only and is not intended to be limiting in any manner or scope. For example, as used in this specification and the appended claims the singular forms "a," "an" and "the" can include plural referents unless the content clearly indicates otherwise. Further, all units, prefixes, and symbols may be denoted in its SI accepted form.

Numeric ranges recited within the specification are inclusive of the numbers defining the range and include each integer within the defined range. Throughout this disclosure, various aspects of this invention are presented in a range format. It should be understood that the description in range format is merely for convenience and brevity and should not be construed as an inflexible limitation on the scope of the invention. Accordingly, the description of a range should be considered to have specifically disclosed all the possible sub-ranges, fractions, and individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6, and decimals and fractions, for example, 1.2, 3.8, 1'$_2$, and 4% This applies regardless of the breadth of the range.

So that the present invention may be more readily understood, certain terms are first defined. Unless defined otherwise, all technical and scientific terms used herein have the same meaning as commonly understood by one of ordinary skill in the art to which embodiments of the invention pertain. Many methods and materials similar, modified, or equivalent to those described herein can be used in the practice of the embodiments of the present invention without undue experimentation, the preferred materials and methods are described herein. In describing and claiming the embodiments of the present invention, the following terminology will be used in accordance with the definitions set out below.

The term "about," as used herein, refers to variation in the numerical quantity that can occur, for example, through typical measuring techniques and equipment, with respect to any quantifiable variable, including, but not limited to, mass, volume, time, distance, wave length, frequency, voltage, current, and electromagnetic field. Further, given solid and liquid handling procedures used in the real world, there is certain inadvertent error and variation that is likely through differences in the manufacture, source, or purity of the ingredients used to make the compositions or carry out the methods and the like. The term "about" also encompasses amounts that differ due to different equilibrium conditions for a composition resulting from a particular initial mixture. The term "about" also encompasses these variations. Whether or not modified by the term "about," the claims include equivalents to the quantities.

The phrase "and/or," when used between elements in a list, is intended to mean either (1) that only a single listed element is present, or (2) that more than one element of the list is present. For example, "A, B, and/or C" indicates that the selection may be A alone; B alone; C alone; A and B; A and C; B and C; or A, B, and C. The phrase "and/or" may be used interchangeably with "at least one of" or "one or more of" the elements in a list.

As used herein, an "effective amount" refers to the amount of agent, such as a probiotic that is sufficient to prevent, treat, reduce and/or ameliorate the symptoms and/or underlying causes of a disorder or disease. In an exemplary aspect, an "effective amount" refers to the amount of probiotic that is sufficient to prevent, inhibit, and/or treat depression, hypertension, stress, anxiety and/or side effects associated with monoamine inhibitors, agonists, or prodrugs, e.g., antidepressants, stimulants, and sedatives. An effective amount of a probiotic is from about $1\times10^3$ to about $1\times10^{12}$ CFUs, more preferably from about $1\times10^5$ to about $1\times10^9$ CFUs, and even more preferably from about $1\times10^5$ to about $1\times10^8$ CFUs. An effective amount of a probiotic may be administered in a single dose or in one or more doses per day. If administered in more than one dose per day, the effective amount may be administered in two doses per day, three doses per day, four doses per day, or more.

The term "microbial community", as used herein, refers to the population of microorganisms inhabiting a local environment within a host animal or human. Such local environments may include, but are not limited to, the skin or "hollow organs." The term "hollow organs", as used herein, refers to organs including, but not limited to, the gastrointestinal tract, oral cavities, and the vagina.

As used herein, "subject" refers to a human or animal. Usually the animal is a vertebrate such as a primate, rodent, domestic animal or game animal. Primates include chimpanzees, cynomologous monkeys, spider monkeys, and macaques, e.g., Rhesus. Rodents, some of which are pocket pets, include mice, rats, woodchucks and hamsters. Other pocket pets include ferrets and rabbits. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. Patient or subject includes any subset of the foregoing, e.g., all of the above, but excluding one or more groups or species such as humans, primates or rodents. In certain embodiments, the subject is a mammal, e.g., a primate or a human. The terms, "patient" and "subject" are used interchangeably herein. More specifically the subject is human. In one aspect, the subject is suffering from maladies that may include, but are not limited to, those bearing signs of localized inflammation, depression, anxiety, insomnia, psychosis, hypertension, Parkinson's disease, fever, fatigue, abdominal pain, abdominal cramping, blood in the stool, reduced appetite, and/or unintended weight loss or weight gain. Subject and host animal or human may be used interchangeably herein.

As used herein, the "alimentary tract" refers to the pathway by which food enters the body of a subject and solid wastes are expelled. The alimentary canal includes, for example, the mouth, pharynx, esophagus, stomach, small intestine, large intestine, and anus.

Also, as used herein, the term "gut" refers to the gastrointestinal tract as well as liver, spleen, pancreas, omentum, and other organs served by the blood supply to and from the gut.

As used herein, the term "administering" refers to the placement of a compound or composition into a subject by a method or route which results in at least partial localization of the compound or composition to the gut or other hollow organ (e.g. oral cavity, vagina) such that a desired effect is produced. A compound or composition described herein can be administered in a human or animal reservoir by any appropriate route known in the art including, but not limited to, oral or parenteral routes, including intravenous, intramuscular, subcutaneous, transdermal, airway (aerosol), pulmonary, nasal, rectal, and topical (including buccal and sublingual) administration.

A probiotic may be administered as a lyophilized powder or in a tablet form. The lyophilized powder may be added to a liquid such as, but not limited to, water or food for ingestion. The tablet may be a chewable tablet. The probiotic may be administered live or heat inactivated dead cells, and in whole or in part. The parts of the probiotic may include cellular components, such as, but not limited to, the DNA or protein which are capable of rendering their beneficial effects, for example a composition comprising PMAT- or OCT-like proteins embedded within a micelle.

Substrates may be administered in any pharmaceutically acceptable formulation such as, but not limited to, a tablet or as part of a composition comprising the substrate and a pharmaceutically acceptable carrier.

Tablets and capsules for administration may be in unit dose form, and may contain conventional excipients such as binding agents, for example syrup, acacia, gelatin, sorbitol, tragacanth, or polyvinyl-pyrrolidone; fillers for example lactose, sugar, maize-starch, calcium phosphate, sorbitol or glycine; tableting lubricant, for example magnesium stearate, talc, polyethylene glycol or silica; disintegrants for example potato starch, or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin hydrogenated edible fats; emulsifying agents, for example lecithin, sorbitan monooleate, polysorbate 80, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavoring or coloring agents.

As used here, the term "pharmaceutically-acceptable carrier" means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) $C_2$-$C_{12}$ alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein.

The phrase "therapeutically-effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment. For example, an amount of a compound administered to a subject that is sufficient to produce a statistically significant, measurable change in at least one symptom of cancer or metastasis.

By "treatment", "prevention" or "amelioration" of an adverse condition is meant delaying or preventing the onset of such a disease or disorder, reversing, alleviating, ameliorating, inhibiting, slowing down or stopping the progression, aggravation or deterioration the progression or severity of a condition associated with such an adverse condition. In one embodiment, at least one symptom of an adverse condition is alleviated by at least 5%, at least 10%, at least 20%, at least 30%, at least 40%, or at least 50%.

The term "dysbiosis", as used herein, refers to a microbial imbalance or maladaptation on or inside the body. Dysbioses involving the gut, for example, have been associated with illnesses, such as inflammatory bowel disease, chronic fatigue syndrome, obesity, cancer, bacterial vaginosis, and colitis.

"Biogenic amines" are biogenic substances with one or more amine groups. For example, they are basic nitrogenous compounds formed mainly by decarboxylation of amino acids or by amination and transamination of aldehydes and ketones. Exemplary biogenic amines include but are not limited to serotonin (5-hydroxytryptamine), histamine, dopamine, norepinephrine, epinephrine, as well as trace amines such as phenethylamines, thyronamine compounds, tryptamine, tyramine and combinations thereof.

"Related substrates" refers to substances which interact with the discovered microbial transporting functions to influence the reuptake, synthesis, and/or extracellular levels of biogenic amines, or are transported in a similar manner as biogenic amines. Exemplary drugs that relate to these capabilities include but are not limited to L-DOPA, Dopamine, Carbidopa, Tryptophan, Fenfluramine, Imipramine (Tofranil™), Clomipramine (Anafranil™), Desipramine (Norpramin™), Nortriptyline (Pamelor™), Fluoxetine (Prozac™), Sertraline (Zoloft™), Paroxetine (Paxil™), Fluvoxamine (Luvox™) Bupropion (Wellbutrin™), Methylphenidate (Ritalin™), phenelzine, tranylcypromine, iproniazid, pargyline, Deprenyl, and similar therapeutic compounds, or combinations thereof.

"Increased fluorescence" refers to a higher relative fluorescence units (RFU) in one sample compared to another. The "sample" may be a strain of a bacterium or fungus. One bacterial or fungal strain may be compared to another strain or a treated strain may be compared with the same, but untreated, strain. The increase in RFU may be about 1.05×, about 1.1×, about 1.2×, about 1.3×, about 1.5×, about 2×, about 3×, about 4×, about 5×, about 6×, about 7×, about 8×, about 9×, about 10× or more.

"Microorganism" refers to an organism or microbe of microscopic, submicroscopic, or ultramicroscopic size that typically consists of a single cell. Examples of microorganisms include bacteria, viruses, parasites, fungi, certain algae, and protozoa. The term "microbial" indicates pertaining to, or characteristic of a microorganism.

"Non-pathogenic bacteria" refer to bacteria that are not capable of causing disease or harmful responses in a host. In some embodiments, non-pathogenic bacteria are commensal bacteria. Examples of non-pathogenic bacteria include, but are not limited to certain strains of *Bacillus* spp., *Bacteroides* spp., *Bifidobacterium* spp., *Brevibacteria* spp., *Clostridium* spp., *Enterococcus* spp., *Escherichia coli*, *Lactobacillus* spp., *Lactococcus* spp., *Saccharomyces* spp., and *Staphylococcus* spp., e.g., *Bacillus coagulans*, *Bacillus subtilis*, *Bacteroides fragilis*, *Bacteroides subtilis*, *Bacteroides thetaiotaomicron*, *Bifidobacterium bifidum*, *Bifidobacterium infantis*, *Bifidobacterium lactis*, *Bifidobacterium longum*, *Clostridium butyricum*, *Enterococcus faecium*, *Lactobacillus acidophilus*, *Lactobacillus bulgaricus*, *Lactobacillus casei*, *Lactobacillus johnsonii*, *Lactobacillus paracasei*, *Lactobacillus plantarum*, *Lactobacillus reuteri*, *Lactobacillus rhamnosus*, and *Lactococcus lactis* (Sonnenbom et al., 2009; Dinleyici et al., 2014; U.S. Pat. Nos. 6,835,376; 6,203,797; 5,589,168; 7,731,976). Naturally pathogenic bacteria may be genetically engineered to provide reduce or eliminate pathogenicity according to standard methods in the art.

The terms "microbiome" or "microbial community", as used interchangeably herein, refer to a population of microorganisms from a particular environment, including the environment of the body or a part of the body. The term is interchangeably used to address the population of microorganisms itself (sometimes referred to as the microbiota), as well as the collective genomes of the microorganisms that reside in the particular environment. The term "environment", as used herein, refers to the surrounding circumstances, conditions, or influences to which a population of microorganisms is exposed. The term is intended to include environments in a subject, such as a human subject.

The term "modulate" or "modulating", as used herein, refers to either increasing or decreasing a trait such as, but not limited to, biogenic amine and related substrate binding or uptake. A trait may be modulated by increasing or decreasing the trait by when compared to non-modulated trait. The trait may be increase by at least about 1.05×, at least about 1.1×, at least about 1.5×, about 2×, at least about 2.5×, at least about 3×, at least about 3.5×, at least about 4×, at least about 4.5×, at least about 5×, at least about 5.5×, at least about 6×, at least about 6.5× at least about 7×, at least about 7.5×, at least about 8×, at least about 8.5× at least about 9×, at least about 9.5×, at least about 10× or more. The trait may be decreased by at least about 5%, at least about 10%, at least about 15%, at least about 20%, at least about 25%, at least about 30%, at least about 35%, at least about 40%, at least about 50%, at least about 60%, at least about 70%, at least about 80%, at least about 90%, or about 100%.

The term "population", as used herein, refers to a plurality of individual organisms, in the context of this invention, the term refers in particular to a collection of organisms of diverse taxonomic affiliation, in particular bacteria.

"Probiotic" is used to refer to live, non-pathogenic microorganisms, e.g., bacteria, which can confer health benefits to a subject organism that contains an appropriate amount of the microorganism. In some embodiments, the subject organism is a mammal. In some embodiments, the subject organism is a human. In some embodiments the host organism is a bird, reptile or fish. Some species, strains, and/or subtypes of non-pathogenic bacteria and yeast are currently recognized as probiotics. Examples of probiotics include, but are not limited to, *Candida* spp., *Debaryomyces* spp., *Debaryomyces* spp., *Kluyveromyces* spp., *Kluyveromyces* spp., *Saccharomyces* spp., *Yarrowia* spp., *Bifidobacteria* spp., *Escherichia coli*, and *Lactobacillus* spp., e.g., *Candida humilis*, *Debaryomyces* hansenii, *Debaryomyces occidentalis*, *Kluyveromyces lactis*, *Kluyveromyces lodderae*, *Kluyveromyces marxianus*, *Saccharomyces cerevisiae*, *Saccharomyces boulardii*, *Yarrowia lipolytica*, *Bifidobacterium bifidum*, *Enterococcus faecium*, *Escherichia coli* strain Nissle, *Lactobacillus acidophilus*, *Lactobacillus bulgaricus*, *Lactobacillus paracasei*, and *Lactobacillus plantarum* (Dinleyici et al., 2014; U.S. Pat. Nos. 5,589,168; 6,203,797; 6,835,376). The probiotic may be a variant or a mutant strain of bacterium (Arthur et al., 2012; Cuevas-Ramos et al., 2010; Olier et al., 2012; Nougayrede et al., 2006). Non-pathogenic bacteria may be genetically engineered to enhance or improve desired biological properties, e.g., survivability. Non-pathogenic bacteria may be genetically engineered to provide probiotic properties. Probiotic bacteria and/or yeast may be genetically engineered to enhance or improve probiotic properties.

The term "sample", as used herein, refers to any sample suitable for analyzing or typing according to the methods of the present invention. A sample may be collected from an organism (e.g., human or other mammal, bird, fish or reptile) and can be in any form, including without limitation a solid material such as a tissue, cells, a cell pellet, a cell extract, or a biopsy, or a biological fluid such as urine, blood, stool, saliva, amniotic fluid, exudate from a region of infection or inflammation, or the like.

The term "sufficient amount of time", as used herein, refers to time it takes for a compound, material, composition comprising a compound of the present invention, or an organism which is effective for producing some desired effect in at least a sub-population of cells.

The term "transporter", as used herein, refers to an integral membrane protein involved in the movement of ions, small molecules, or macromolecules, such as, but not limited to, proteins, across a membrane. The transporter may assist in the movement of substances by facilitated diffusion or active transport.

The term "uptake capability profile", as used herein, refers to the presence and capabilities of biogenic amine PMAT- and/or OCT-like transporters in a population. The term "target uptake capability profile", as used here, refers to a modulated uptake capability profile that aid in treatment of an adverse condition. For example, an uptake capability profile may indicate a subject's microbiome contains PMAT- but not OCT-like transporters, while the target uptake capability profile may include both PMAT- and OCT-like transporters.

As used herein, the term "substantially free" refers to compositions completely lacking the component or having such a small amount of the component that the component does not affect the effectiveness of the composition. The component may be present as an impurity or as a contaminant.

The term "richness and diversity", as used herein, refers to species richness and species diversity. Species richness is the number of different species represented in a given population. Species richness is a count of the number of species and does not take the abundance or relative abundance distribution into consideration. Species diversity is also a measure of the number of different species in a population, but is calculated using species richness, taxonomic or phylogenetic diversity, and species evenness.

Methods for Characterizing a Microbiome and/or Probiotic Strains and Identifying Therapeutic Measures In one aspect, the present invention involves a method for selecting or identifying probiotic strains capable of uptake and/or transport of biogenic amines and/or related-drugs. In one aspect, the method includes screening for the presence of at least one transporter involved in the uptake of biogenic amines. Detecting uptake may be performed by, but not limited to, contacting cells with a biogenic amine and/or a related substrate, then measuring uptake, such as, but not limited to, by measuring a fluorescent response; assaying the change in the concentration of the substrate in the media or within the cells using high-performance liquid chromatography (HPLC); through measurements of cellular uptake of labeled substrates, where the label may include, but not limited to, a fluorophore or radio label; through immunohistochemistry, Western blotting, or ELISA; or using various microscopy techniques.

For example, a fluorophore, such as but not limited to, IDT307 (4-[p-(Dimethylamino)phenyl]-1-methylpyridinium iodide), ASP$^+$ ([4-(4-(diethylamino)styryl)-N-methylpyridinium iodide]), APP$^+$, and 7-hydroxycoumains, such as, but not limited to, AGH093, FFN202, Mini101, FFN102, Mini103, AGH113, and/or other variants known in the art may be contacted with cells for a sufficient amount of time; followed by detecting the ability of said fluorophore to enter said strain as reflected by increased fluorescence when compared to a probiotic strain which is not capable of transporting the fluorophore. A sufficient amount of time for the fluorophore to be in contact with the cells may range from between about 10 seconds to about 25 hours, between about 1 minute and about 25 hours, between about 1 minute and about 9 hours, between about 30 minutes and about 9 hours, between about 1 minutes and about 8 hours, between about 30 minutes and about 8 hours, between about 1 minute and about 7 hours, between about 30 minutes and about 7 hours, between about 1 minute and about 24 hours, or between 30 minutes and 24 hours.

If the probiotic to be screened is bacterial, it may be either adherent or planktonic bacteria. Preferably, the probiotic strain is adherent. If the strain is an adherent bacterial strain, the strain is may be allowed a sufficient amount of time to form a biofilm in culture prior to contacting said strain with a substrate, such as a radiolabeled compound or fluorophore. A sufficient time to form a biofilm may be up to about 1 hour, up to about 2 hours, up to about 3 hours, up to about 4 hours, up to about 5 hours, up to about 6 hours, up to about 12 hours, up to about 24 hours, up to about 36 hours.

Moreover, the present invention includes methods of selecting and/or identifying which are standard and known in the art for detecting microbial protein expression, specifically, expression of PMAT- and/or OCT-like capabilities. Such methods include, in non-limiting examples, Western blotting, sequencing, or use of luminescent reporter systems. Additionally, the present invention includes methods standard and known in the art of selection and/or identifying based on the genotype or RNA expression, such as, but not limited to, sequencing, polymerase chain reaction followed by sequencing or restriction fragment length polymorphism, quantitative polymerase chain reaction, or by high-throughput sequencing.

In one embodiment, the methods of the present invention provide screening of a subject's microbiome for the presence or absence of bacterial or fungal strains expressing a transporter capable of uptake of biogenic amines or related substrates. Biological samples are preferably received from subjects in a non-invasive manner. In variations, non-invasive manners of sample reception can use any one or more of: a permeable substrate (e.g., a swab configured to wipe a region of a subject's body, toilet paper, a sponge, etc.), a non-permeable substrate (e.g., a slide, tape, etc.), a container (e.g., vial, tube, bag, etc.) configured to receive a sample from a region of a subject's body, and any other suitable sample-reception element. In a specific example, samples can be collected from one or more of a subject's nose, skin, genitals, mouth, and gut in anon-invasive manner (e.g., using a swab and a vial). However, one or more biological samples of the set of biological samples can additionally or alternatively be received in a semi-invasive manner or an invasive manner. In variations, invasive manners of sample reception can use any one or more of: a needle, a syringe, a biopsy element, a lance, and any other suitable instrument for collection of a sample in a semi-invasive or invasive manner. In specific examples, samples can comprise blood samples, plasma/serum samples (e.g., to enable extraction of cell-free DNA), and tissue samples.

Growth and expansion of bacterial or fungal strains to be screened can be accomplished by standard methods known those of skill in the art. For example, probiotics and/or strains obtained from a subject are grown for a sufficient amount of time, for example, growth may be for about 10, about 11, about 12, about 13, about 14, about 15, about 16, about 17, about 18, about 19, about 20, or about 24 hours. Incubation may be done at temperatures ranging from about 15° C. to about 42° C., preferably about 37° C. Adjusting temperatures may be done to influence certain traits, for example growth rate or uptake of biogenic amines, with lower temperatures generally slowing metabolic and catabolic rates, of said strains. Additionally, one skilled in the art will know or can readily determine if incubation of specific strains may be done under aerobic or anaerobic conditions.

Once a sufficient number of bacteria or fungus is obtained, the culture medium is removed and a sufficient amount of a probe, such as fluorescent probes (e.g. about 1 to about 200 μM of ASP$^+$ and/or IDT307) are added. A sufficient number of a microbe and a sufficient amount of probe will be known or readily determinable by those skilled in the art. The samples are then placed into a system capable of detecting the probe, such as a plate reader, and read continuously. Detecting the ability of said probe to enter said strain is reflected by increased signal, for example an increased fluorescence, when compared to a probiotic strain which does not express a transporter capable of binding or transporting the biogenic amine and/or related substrate.

In one embodiment, the methods of the present invention are used to diagnose, and thereby predict clinical therapy in subjects suffering from conditions such as depression. In one aspect, the methods include screening the microbiome of the subject to determine the presence or absence of bacterial or fungal strains in the subjects' microbiome which possess the capability to influence the availability of a biogenic amine and or related substrate. For example, if the subject's microbiome did not contain strains capable of PMAT- or OCT-like biogenic amine uptake, the subject may be given a lower amount of biogenic amine or a related substrate to obtain a therapeutic-effect amount. Alternatively, the subject may have their microbiome modulated by administering a composition comprising of probiotic microbes capable of PMAT- and/or OCT-like uptake to reduce biogenic amines within the gut, which may be over expressed due to an ailment such as, but not limited to, stress. Conversely, if the subject's microbiome is cable of PMAT- or OCT-like uptake, the subject may be given more biogenic amine or a related substrate to obtain a therapeutic-effective amount, or a transport inhibitor such as, but not limited to, decynium-22 or fluoxetine.

In another embodiment, the screening and targeting of the neurochemical transporters described according to embodiments of the invention provide targets for various therapeutic measures. Such therapeutic measures can include drug applications, other therapeutic applications including general health and well-being, and/or nutrition. As one skilled in the art recognizes, there is a biochemical signaling in the gut-brain axis joining the microbiota, the alimentary tract (including the gastrointestinal tract) and the central nervous system. The gut-brain axis includes the microbiota in the alimentary tract, central nervous system, neuroendocrine and neuroimmune systems (e.g. hypothalamic-pituitary-adrenal axis), sympathetic and parasympathetic arms of the autonomic nervous system, and the gut microbiota. Beneficially, the therapeutic measures are suitable for adjuvant treatment of various therapeutic treatments of pathologies, improvement in nutrition, such as feeding efficiency and weight management.

In another embodiment, the screening and targeting of the neurochemical transporters capable of biogenic amine uptake described according to embodiments of the invention provide for compounds, such as, but not limited to biogenic amines, related substrates including known medications in clinical use and/or fluorophores which do not interact with the monoamine transporters in the microbiome. After screening for and identifying strains capable of monoamine transport, various biogenic amines and/or related substrates may be contacted with the cells at various concentrations. It may then be determined which compounds may interact with the microbiome by measuring changes in uptake of biogenic amines and/or related substrates, which subset of uptake transport the microbiome is capable of, and at what inocula, concentrations or doses. This would allow the selection of drugs and other compounds that may have a therapeutic effect on a subject without being sequestered by the microbiome. For example, screening the microbiome for PMAT- and/or OCT-like transporting functions; contacting the microbes having PMAT- and/or OCT-like capabilities with biogenic amines and/or related substrates; and then screening for the biogenic amines or related substrates which are not sequestered into the microbes. Screening may be done by any method known in the art, including fluorescence, radiochemical detection, HPLC, Western Blot, ELISA, or immunohistochemistry. These and other applications will be readily apparent based on the disclosure herein.

Methods and Compositions for Targeting Probiotic PMAT- and OCT-Like Capabilities In one embodiment of the invention beneficially provides at least partial inhibition of probiotic-expressed biogenic amine transport capabilities. In one aspect, the probiotic transport capabilities are targeted through chemical inhibitors. For example, such inhibitors include but are not limited to, cimetidine, decynium-22, dipyridamole, quinidine, quinine, tryptamine, and verapamil. The biogenic amine uptake in the natural microbiota of a subject represent an important pharmacological target for both wellness (i.e. managing stress) and inflammatory conditions. The amount of chemical inhibitor needed to effect at least partial inhibition of biogenic amine uptake is known or readily determined by one of ordinary skill in the art. For example, several drugs in clinical practice, such as, but not limited to, particular classes of anti-anxiety and antidepressant drugs, are based on the use of selective serotonin reuptake inhibitors (SSRIs). The present invention provides methods and compositions which detect the actions of SSRIs on the microbiota in the gut of a subject in need thereof by targeting the microbial PMAT- and/or OCT-like uptake thereby making bioactive substrates normally transported into particular microbes more available in the gut lumen to treat the ailment.

In one embodiment one or more inhibitors targeting a probiotic biogenic amine uptake as identified in the present invention is administered prior to administration of a biogenic amine related drug. In another embodiment, the one or more inhibitors targeting a probiotic biogenic amine uptake identified in the present invention is administered concurrently or subsequent to administration of a biogenic amine related drug. Inhibition of the uptake may result in a slowed initial uptake to a complete block of uptake of biogenic amines or related substrates into microbial cells. Inhibition may be measured by any method known in the art for measuring uptake, including, but not limited to, fluorescence, radiochemical detection, HPLC, Western Blot, immunohistochemistry, or ELISA. For example, inhibition may be assayed an increased fluorescence in untreated microbes compared to inhibitor-treated microbes or by an increased concentration of biogenic amines and/or related substrates remaining in the media over time. Inhibition may result in a decreased uptake by at least about 5%, at least about 10%, at least about 15%, at least about 20%, at least about 25%, at least about 30%, at least about 35%, at least about 40%, at least about 50%, at least about 60%, at least about 70%, at least about 80%, at least about 90%, or about 100%.

EXAMPLES

Example 1: Identification of PMAT-Like

To demonstrate the presence of at least one uptake2 system is present in the gut microbiome, the PMAT-like uptake was assessed in Lactobacillus strains.

A neurotransmitter transporter uptake assay kit system (Molecular Devices Kit #R6138, Sunnyvale, CA) was used. The kit was used according to the instructions with the exception of the identified solution (a basal salt solution, e.g. Hank's Balanced Salt Solution or HBSS) for culturing the cells. In this regard, the inventors have identified the use of HBSS with microbial samples is inoperable. Instead, a more complete medium, deMan, Rogosa and Sharpe (MRS), was used in its place. Other suitable solutions include, for example, phenol red free medium such as Iscove's Modified Dulbecco's Medium (IMDM) or Dulbecco's Modified Eagle Medium (DMEM). Furthermore, other suitable kits include Molecular Devices Kit #R8173 and #R8174. A range of probiotic strains was employed and examined with the kit. It should be noted that the kit does not state that it can be used with bacterial cells as it has only been validated for use on mammalian cells and has never been tried with bacterial cells before. The probiotics included those sent by Metagenics, Inc., from ATCC, or part of the inventor's laboratory collection.

Probiotics were grown overnight in flat-bottomed 96-well plates in MRS medium. The probiotics that were utilized were capable of forming biofilms to varying degrees. The use of a biofilm forming probiotic is preferred in the adapted Molecular Devices assay as the plate reader measures fluorescence from the bottom of the well. There is nothing in this disclosure that should be construed that the probiotic needs to be a biofilm-producing strain as it is fully anticipated that non-biofilm producing probiotics can also possess biogenic amine uptake systems and that other assays such as, but not limited to, tube-based assays could also be used.

Following overnight incubation at 37° C. in an anaerobic environment, the medium in each well was carefully removed in order to not overtly disturb the biofilm and the assay reagent, IDT307 fluorophore, was added per the manufacturer's protocol. The plate was then placed into a BioTek Synergy H1 plate reader at 37° C. and read continuously for a total of 30 minutes. Subsequent experiments have expanded that range to 60 minutes up to 24 hours.

Figure 7:
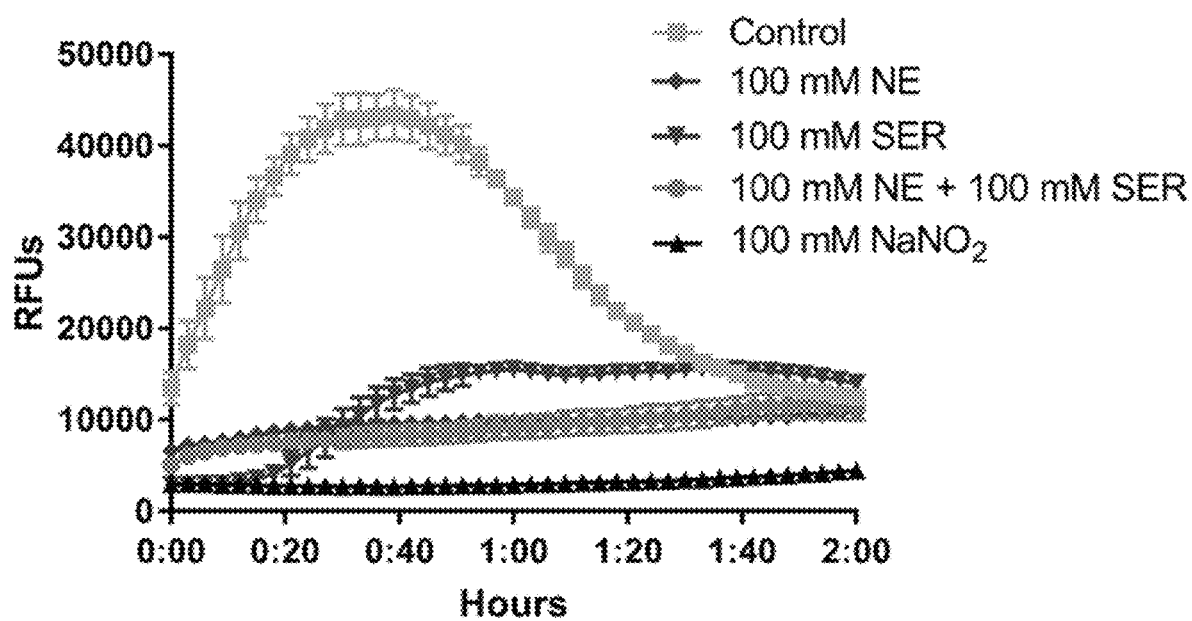
FIG. 7 shows the ability of natural substrates and the metabolic inhibitor nitrate to inhibit fluorophore uptake into *L. salivarius* biofilms. *L. salivarius* biofilms in flat clear-bottomed 96 well microplates were prepared as described in Example 4. Following 6-hours incubation, the medium in each well was gently removed and 100 µl of a pre-warmed solution of the natural transporter substrates norepinephrine (NE) and serotonin (SER), alone or in equimolar combination, was added to appropriate wells to achieve a final biogenic amine concentration of 100 mM. The metabolic inhibitor sodium nitrite ($NaNO_2$) was also added to appropriate wells to achieve a final concentration of 100 mM. The plate was then immediately placed back into a 37° C. incubator for 30 minutes after which time it was removed and 100 µl of pre-warmed fluorophore was added to appropriate wells. The plate was then immediately placed into the fluorescence plate reader and measured at 37° C. Results represent mean±S.E.M of triplicate wells and are representative of at least two separate experiments. For some points, the S.E.M. error bars are obscured by the symbol.
Figure 8A:
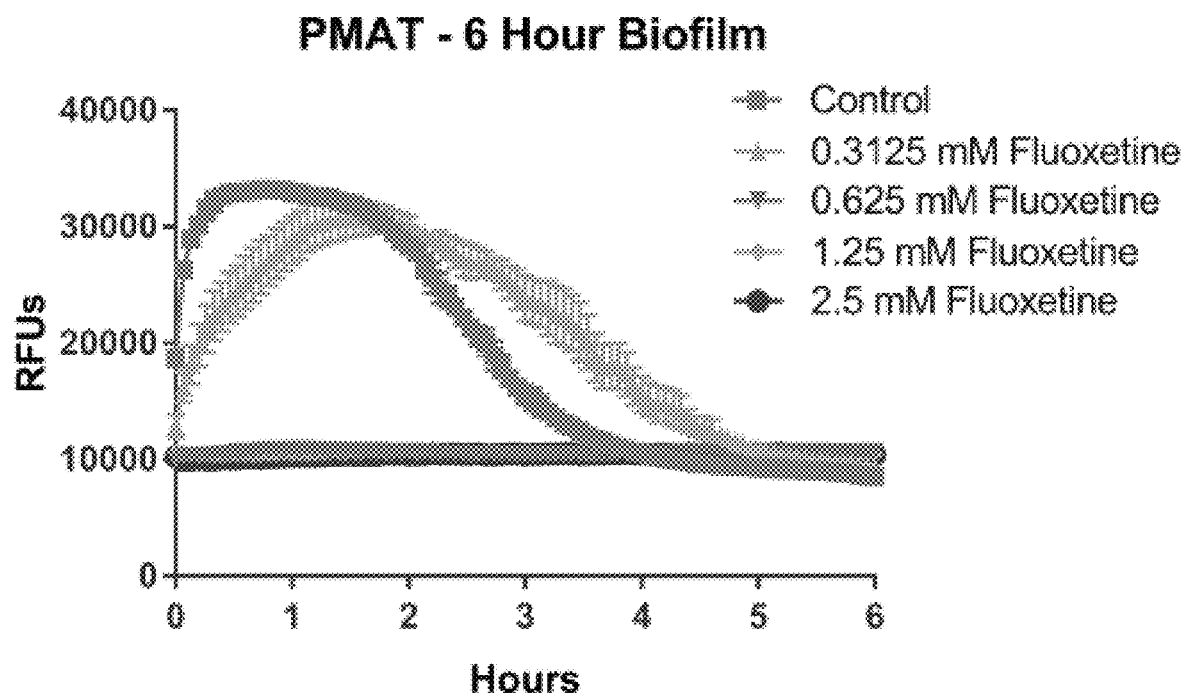
FIG. 8A is a graphical representation of the concentration-dependent inhibition of IDT307 (probe for PMAT-like) uptake by various concentrations of fluoxetine into early biofilms (6-hour incubation).
Figure 8B:
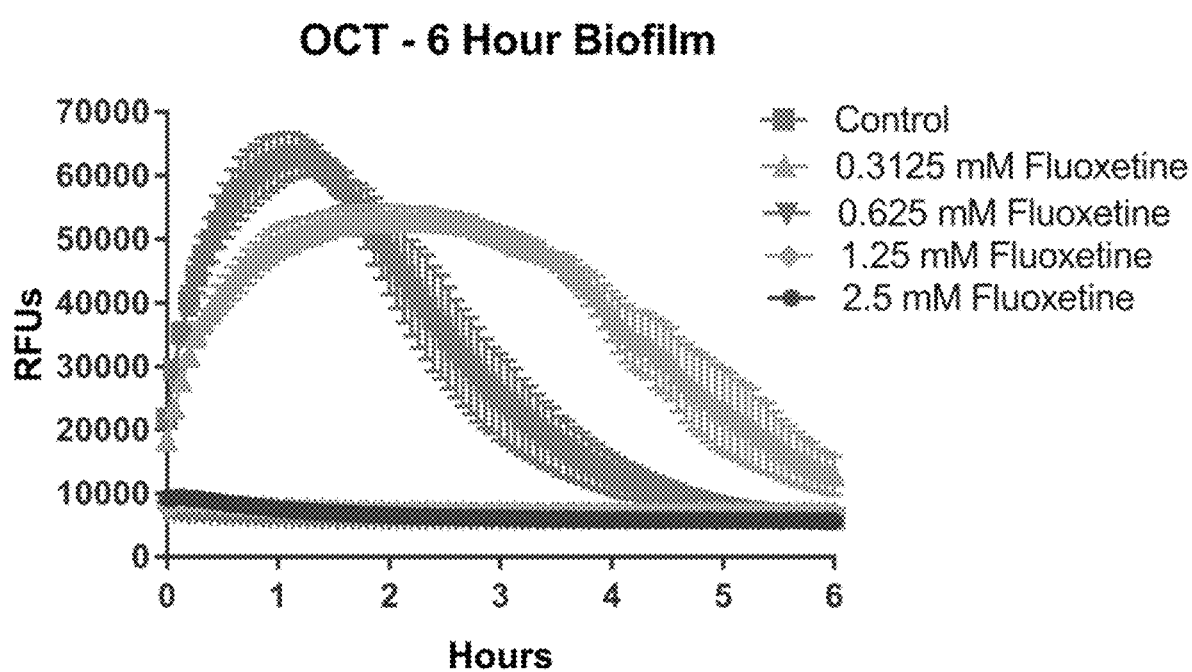
FIG. 8B is a graphical representation of the concentration-dependent inhibition of ASP$^+$ (probe for OCT-like) uptake by various concentrations of fluoxetine into early *L. salivarius* biofilms.
Figure 8C:
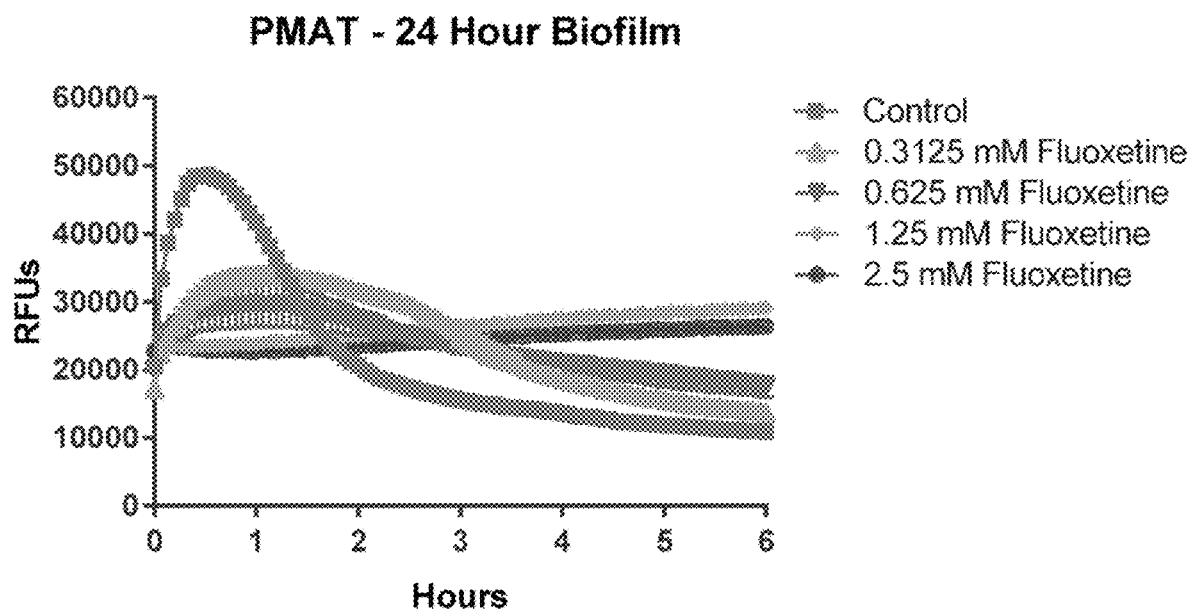
FIG. 8C is a graphical representation of the concentration-dependent inhibition of PMAT uptake by various concentrations of fluoxetine into late (24-hour incubation) *L. salivarious* biofilms.
Figure 8D:
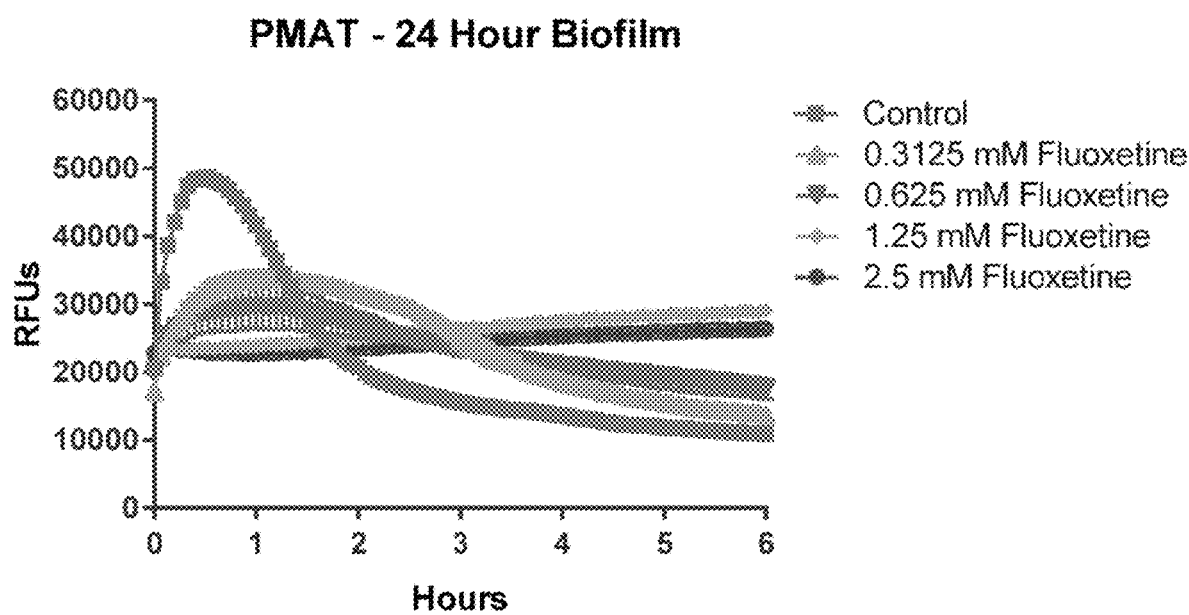
FIG. 8D is a graphical representation of the concentration-dependent inhibition of ASP$^+$ uptake by various concentrations of fluoxetine into late *L. salivarious* biofilms. *L. salivarius* biofilms in flat clear-bottomed 96 well microplates were prepared as described in Example 4 for each of FIGS. 8A-8D. Following either early or late biofilm formation, the medium in each well was gently removed and 100 µl of pre-warmed solution of fluoxetine dissolved in IMDM in the increasing concentrations shown in FIGS. 8A-8D or IMDM alone was added to the appropriate wells. The plate was then immediately placed back into a 37° C. incubator for 30 minutes after which time it was removed and 100 µl of pre-warmed fluorophore, either PMAT or ASP$^+$, was added to the appropriate wells, the plate was then immediately placed into the fluorescence reader and measured at 37° C. Results represent mean±S.E.M. of triplicate wells and are representative of at least two separate experiments. For some points, the S.E.M. error bars are obscured by the symbol.

As shown in the FIG. 7, *Lactobacillus salivarius* demonstrated the presence of a biogenic amine uptake capability analogous to mammalian transporters for the neurotransmitters serotonin, dopamine and norepinephrine. These are designated, respectively, as the SERT, DAT, and NET transporters in mammalian drug discovery. Further, as shown in the FIG. 1, *L. helveticus*, which is a probiotic extensively used in the medical and food industry, does not possess these transport functionalities.

As shown in FIG. 1, the existence of a PMAT-like uptake function has been shown in at least one probiotic strain. This provides a screening tool for selection of probiotics for medical usage in animals and humans.

Example 2: Identification of OCT-Like Capability

To determine if an additional uptake2 system was present in gut microbes, OCT-like capability was assayed in *Lactobacillus* strains.

The fluorophore $ASP^+$[4-(4-(diethylamino)styryl)-N-methylpyridinium iodide] was obtained from Sigma Chemical Company (Sigma #D4318) and used as described in Duan et al., Drug Metabolism and Disposition, volume 43, pages 1773-1780, 2015 (herein incorporated by reference) with a slight modification in the ratio of $ASP^+$ and Trypan blue used. To demonstrate specificity of the transport capability, a known OCT blocker, decynium-22 (D-22, Sigma, #323764) was employed.

It should be noted that none of the above chemicals or methods have ever been used with bacterial cells before to examine transport functionality related to biogenic amine uptake. Published reports utilizing such chemicals have been solely restricted to eukaryotic cells from mammals.

The approach utilized was the same as that described in Example 1 with the exception that $ASP^+$ was used instead of the Molecular Devices IDT307 fluorophore which is used to demonstrate PMAT activity. In brief, probiotics were grown overnight in flat-bottomed 96-well plates in MRS medium. The probiotics that were utilized were capable of forming biofilms to varying degrees. The use of a biofilm forming probiotic is beneficial to the assay as the plate reader used measures fluorescence from the bottom of the well. There is nothing in this disclosure that should be construed that the probiotic needs to be a biofilm-producing strain as it is fully anticipated that non-biofilm producing probiotics can also possess biogenic amine uptake systems and that other methods, such as, but not limited to, tube-based assays could also be used.

Following overnight incubation at 37° C. in an aerobic environment, the medium in each well was carefully removed in order to not overtly disturb the biofilm and control medium (IMDM, Life Technologies, #21056023) was added and the plate incubated for a further 20 minutes at 37° C. in an aerobic environment. Next, $ASP^+$ fluorophore in IMDM was added and the plate was then placed into a BioTek Synergy H1 plate reader at 37° C. and read continuously for a total of 6 hours.

Figure 2:
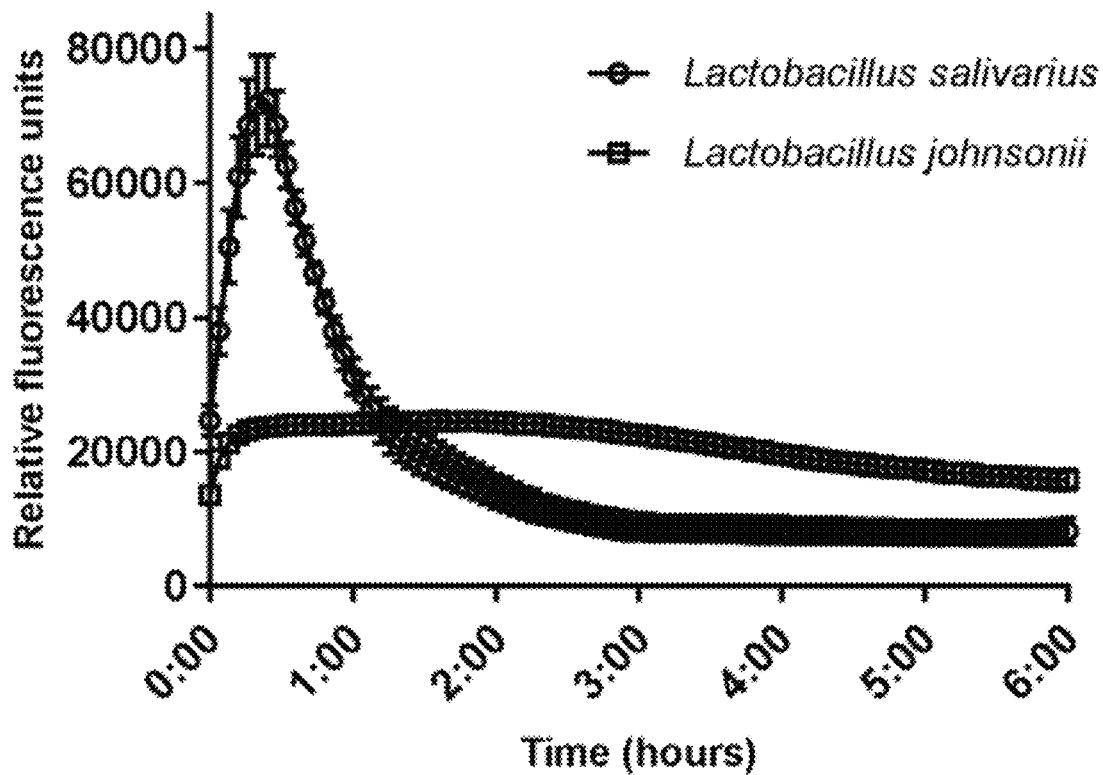
FIG. 2 shows the identification of OCT-like transport in *L. salivarius*

As shown in FIG. 2, *L. salivarius* (obtained from a primate vaginal specimen) showed the presence of a robust OCT-like capability whereas *Lactobacillus johnsonii* (obtained from American Type Culture Collection, #33200) did not. This demonstration that an OCT-like capability is present in some, but not all, Lactobacilli is similar to what has been described for the prevalence of PMAT-like capability in various strains of Lactobacilli. This example further demonstrates a method by which to detect those probiotic strains that may be of greatest benefit for use in the host using the presence of an OCT-like transport capability.

Figure 3:
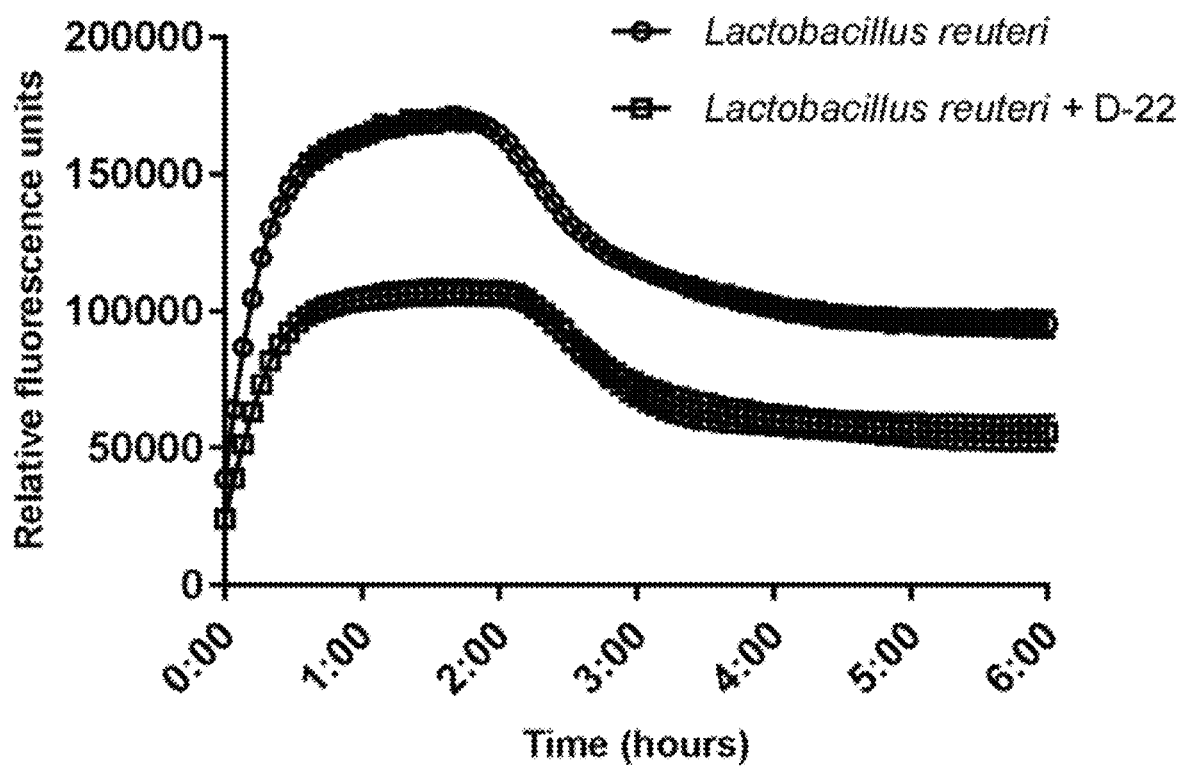
FIG. 3 shows the ability to block OCT-like transport through treatment with D-22.

To verify if OCT-like uptake was responsible for the influx of $ASP^+$ in Lactobacilli, *L. reuteri* was pre-treated with D-22, an OCT inhibitor. In brief, Lactobacilli *reuteri* (obtained from American Type Culture Collection, #23272) were grown overnight at 37° C. in an aerobic environment in flat-bottomed 96-well plates in MRS medium. Following overnight incubation, the medium in each well was carefully removed in order to not overtly disturb the biofilm and a final concentration of 20 μM D-22 dissolved in IMDM or control medium was added. The plate was then incubated for 20 minutes at 37° C. in an aerobic environment. Next, ASP+ fluorophore dissolved in IMDM was added and the plate was then placed into a BioTek Synergy H1 plate reader at 37° C. and read continuously for a total of 6 hours. As shown in FIG. 3, the presence of D-22 reduced the ability of the ASP+ fluorophore to enter into the cells as reflected by decreased fluorescence at all time points. This demonstrates that indeed the transporter capability identified by ASP+ is an OCT-based system.

There is nothing in this disclosure that demonstrates that the presence of either a PMAT- or OCT-based transporter systems are restricted to the probiotic genus Lactobacilli. It is fully anticipated that these transporter systems will also be found in other genera of probiotics.

Probiotic bacteria, such as those belonging to Lactobacilli spp., can possess OCT-like as well as PMAT-like capabilities mediating the uptake of biogenic amines and related substrates that can be targeted to influence host physiology and brain function in veterinary and human clinical practice.

Example 3: Screening of Probiotic Strains

In order to further show the importance of being able to screen specific strains of the gut microbiome, various strains of Lactobacilli were isolated from a variety of sources, including from a number of different animal species. The strains were screened to determine if they were positive or negative for either PMAT-like or OCT-like capabilities:

| Genus/species | Lyte lab # | Origin | Results |
|---|---|---|---|
| 1. L. reuteri | ML1004 | ATCC strain | YES |
| 2. L. reuteri | ML1013 | ATCC type strain | YES |
| 3. L. salivarius | ML1014 | UCC-118 probiotic | YES |
| 4. L. crispatus | ML1018 | Porcine intestinal scraping | NO |
| 5. L. salivarius | ML1019 | Porcine intestinal scraping | YES |
| 6. L. reuteri | ML1020 | Porcine intestinal scraping | YES |
| 7. L. reuteri | ML1022 | Porcine intestinal scraping | YES |
| 8. L. salivarius | ML1031 | Monkey vaginal swab | YES |
| 9. L. murinus | ML1034 | Monkey vaginal swab | NO |
| 10. L. salivarius | ML1036 | Monkey vaginal swab | YES |
| 11. L. murinus | ML1038 | Monkey vaginal swab | NO |
| 12. L. salivarius | ML1042 | ATCC type strain | YES |
| 13. L. brevis | ML1043 | ATCC strain | YES |
| 14. L. rhamnosus | ML1046 | Commercial probiotic | YES |
| 15. L. rhamnosus | ML1052 | Commercial probiotic | NO |
| 16. L. helveticus | ML1054 | Commercial probiotic | YES |
| 17. L. johnsonii | ML1055 | ATCC strain | NO |
| 18. L. casei | ML1065 | Commercial probiotic | NO |
| 19. L. salivarius | ML1067 | ARS strain | YES |
| 20. L. reuteri | ML1069 | ARS strain | NO |
| 21. L. reuteri | ML1070 | ARS strain | NO |

Example 4

To further validate the methods, various strains of Lactobacillus were tested for the detection of PMAT- and OCT-like uptake capability under various conditions, including the length of time for biofilm formation and incubation temperature.

Materials and Methods

Bacterial Strains, Culture Conditions and Reagents

L. salivarius (ATCC type strain #11741) and L. johnsonii (ATCC type strain #11506) were originally obtained from the American Type Culture Collection (Bethesda, MD) and maintained as frozen stocks. L. rhamnosus and a combination of L. rhamnosus and L. johnsonii were also tested. Reconfirmation of all strain identities prior to initiation of experiments was performed using MALDI-TOF (Bruker Inc., Billerica, MA, USA). Cultures were grown in Lactobacilli MRS broth (product #288130, Becton-Dickinson, Franklin Lakes, NJ, USA) from frozen stock the previous night at 37° C. in static culture in a 37° C. humidified incubator. 4-(4-Diethylaminostyryl)-1-methylpyridinium iodide (ASP+; product #D-3418) and other drugs and chemicals were obtained from Sigma-Aldrich (St. Louis, MO) and dissolved in double distilled water prior to use. Decynium-22 (product #D4486) was purchased from TCI Chemicals (Portland, OR, USA) and was prepared in ethanol with further dilution to a final concentration in 0.2% ethanol in experiments. All prepared solutions were sterile filtered prior to use.

PMAT and OCT Fluorescence-Based Assays

For measurement of PMAT-like function, the IDT307 fluorophore-based Neurotransmitter Uptake Assay Kit (product #R8173, Molecular Devices, Sunnyvale, CA, USA) was used with modification. As it is intended for studies with mammalian cells, the kit recommends the use of phenol red-free Hank's Balanced Salt Solution (HBSS). Phenol red-free Iscove's Modified Dulbecco's Medium (IMDM; product #21056-023, Life Technologies, Carlsbad, CA, USA) was substituted for HBSS. Preliminary work showed that no transporter activity in bacterial biofilms could be detected with the use of HBSS (discussed further in Results section). IMDM was selected as it is a nutrient-rich, protein-free medium used in tissue culture that allows for robust growth of a wide variety of bacterial species in the absence of any protein additives common to most microbiology media. Similar tissue culture media, such as Fluoro-Brite DMEM (product #A1896701; Life Technologies), produced similar results to those obtained with IMDM (data not shown).

At the start of the assay, 0.2 ml of stationary phase overnight bacterial growth was inoculated into 9.8 ml of pre-warmed MRS, thoroughly mixed, and 0.2 ml aliquots added to individual wells of Corning flat clear-bottomed 96 well microplates (product #3904, Corning, Inc., Corning, NY, USA). Plates were then placed into a 37° C. humidified incubator. Following static incubation for either 6 or 24 hours, plates were removed from the incubator and the well supernatants were gently removed leaving the bacterial biofilm intact on the bottom surface of the individual clear plate wells. Subsequently, the PMAT-specific fluorophore IDT307 (Molecular Devices) or the OCT-specific fluorophore ASP+ (Sigma-Aldrich) dissolved in IMDM and pre-warmed to 37° C. was gently added to appropriate wells (added along the well side so as not to disturb the biofilm). The plate was immediately placed into a BioTek Synergy H1 reader (Winooski, VT, USA) and measured using Gen5 software at the time intervals shown in the FIGS. 4-7. All assays were done at 37° C. unless otherwise noted and reads were performed as bottom fluorescence in relative fluorescence units (RFU). For IDT307, the chemical and masking dye were supplied pre-measured and the amount of IMDM used as a diluent was the same as indicated for the use of HBSS. For ASP+, the dye and masking solution were prepared as previously reported in Duan H, et al. Potent and Selective Inhibition of Plasma Membrane Monoamine Transporter by HIV Protease Inhibitors. Drug Metab Dispos.

2015; 43(11):1773-80, herein incorporated by reference, with the minor modification that the fluorophore/masking dye combination were prepared as follows: 100 µl of a 2 mg ASP+ stock solution per ml of distilled water was first added to 9.9 ml of IMDM and mixed, followed by the addition of 10 µl of a 10 mM Trypan blue solution. The excitation/emission wavelengths used for IDT307 and ASP+, respectively, were 440 nm/520 nm and 475 nm/609 nm.

As indicated above, IMDM was employed for the preparation of both the IDT307 and ASP+ fluorophores. This was in place of HBSS as the fluorophore diluent since preliminary experiments utilizing HBSS for the preparation of IDT307 did not yield measurable levels of fluorophore uptake.

Results

Figure 4A:
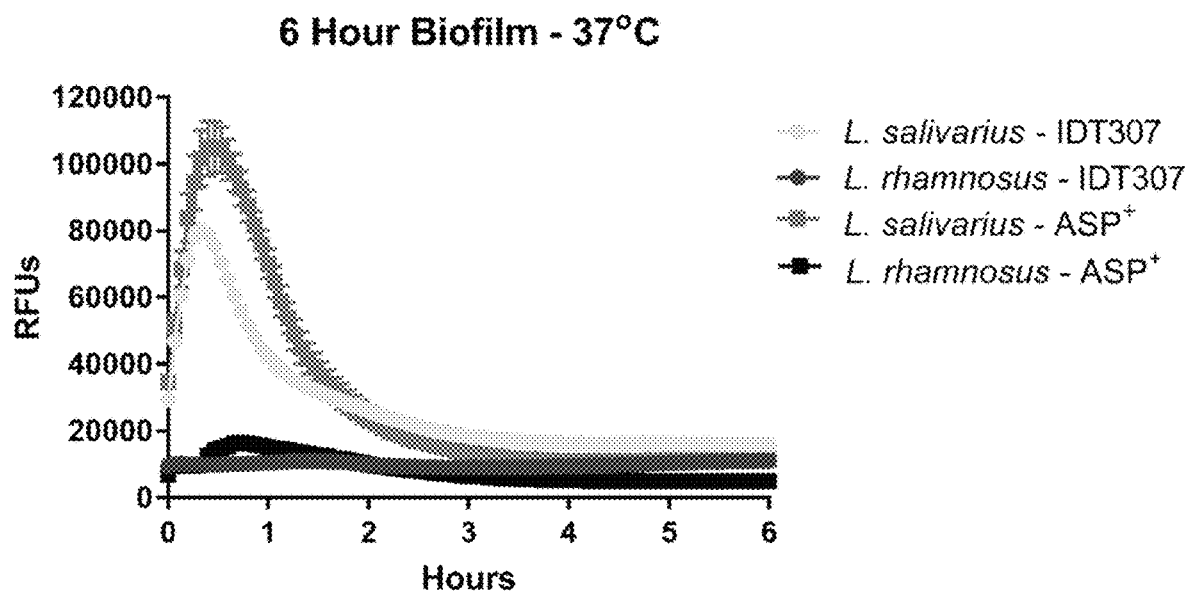
FIG. 4A is a graphical representation of the uptake of transporter fluorophore reporters, either IDT307 (probe for PMAT-like) or ASP$^+$ (probe for OCT-like), following a 6-hour incubation at 37° C. of *L. salivarius* or *L. rhamnosus* to promote early biofilm formation in flat clear-bottomed 96-well microplates were prepared as described in Example 4.
Figure 4B:
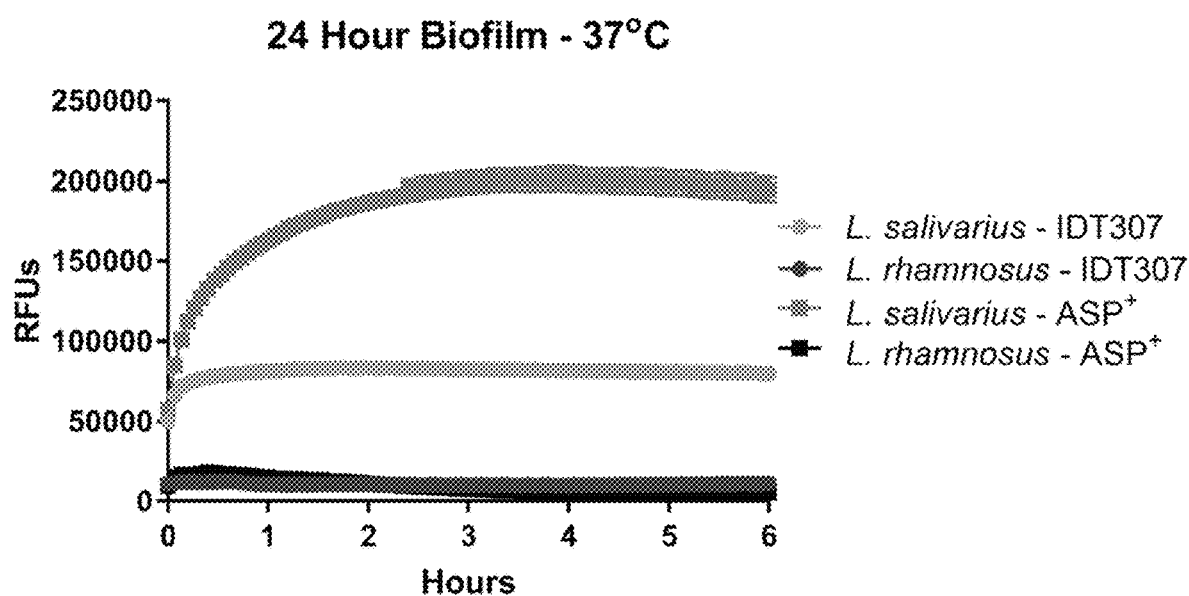
FIG. 4B is a graphical representation of the uptake of IDT307 or ASP$^+$ following a 24-hour incubation at 37° C. of *L. salivarius* or *L. rhamnosus* to promote established biofilm formation in flat clear-bottomed 96-well microplates were prepared as described in Example 4.
Figure 4C:
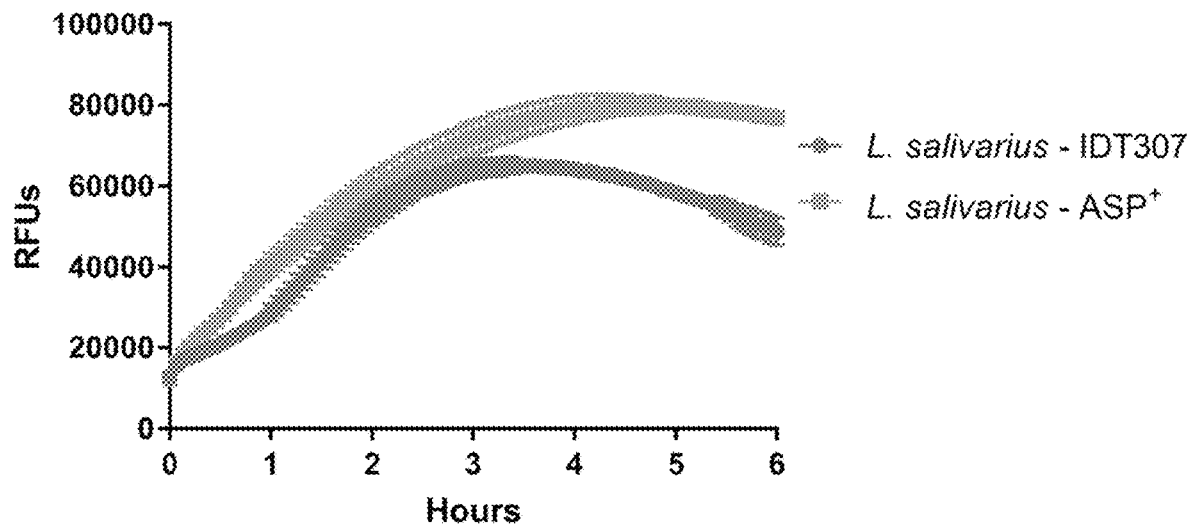
FIG. 4C is a graphical representation of the uptake of IDT307 or ASP$^+$ following a 6-hour incubation at 25° C. of *L. salivarius* to promote early biofilm formation in flat clear-bottomed 96-well microplates were prepared as described in Example 4.
Figure 4D:
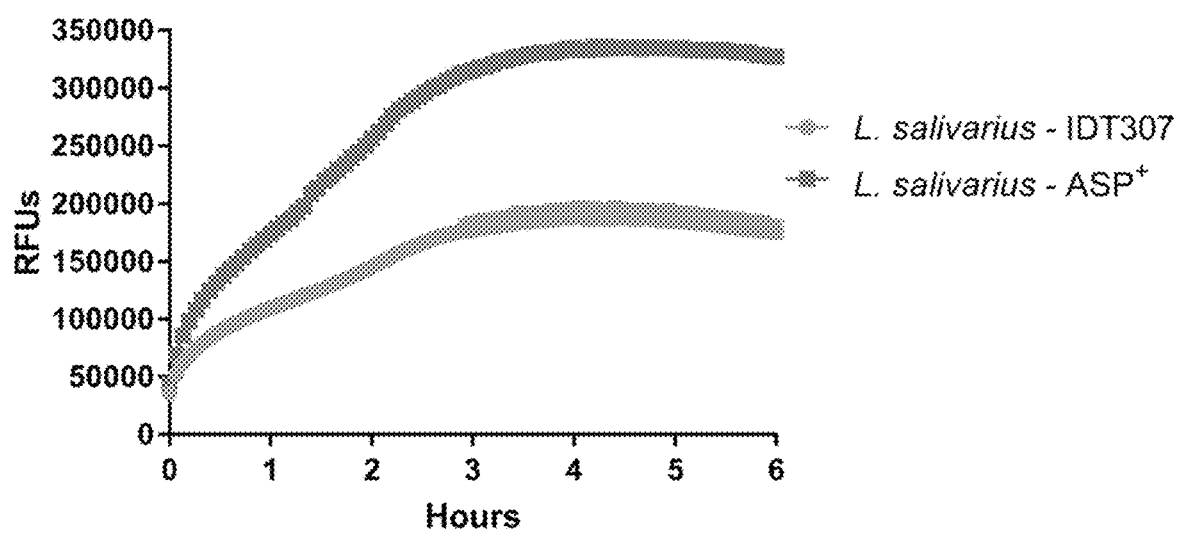
FIG. 4D is a graphical representation of the uptake of IDT307 or ASP$^+$ after a 24-hour incubation at 25° C. to promote formation of an established biofilm in a flat clear-bottomed 96-well microplaces were prepared as described in Example 4. For FIGS. 4A and 4B, fluorophore solutions were pre-warmed and changes in relative fluorescence units (RFU) in each well of the plate were measured at 37° C. over a six-hour time interval. For FIGS. 4C and 4D, the plate was removed from the incubator and placed on a bench-top surface for 1 hour to allow it to reach room temperature prior to fluorophore addition of the at room temperature. Following fluorophore addition, RFUs were measured in the plate at 25° C. over a six-hour time interval. Results represent mean±S.E.M of quadruplicate wells and are representative of a minimum of three separate experiments. For some points, the S.E.M. error bars are obscured by the symbol.
Figure 5A:
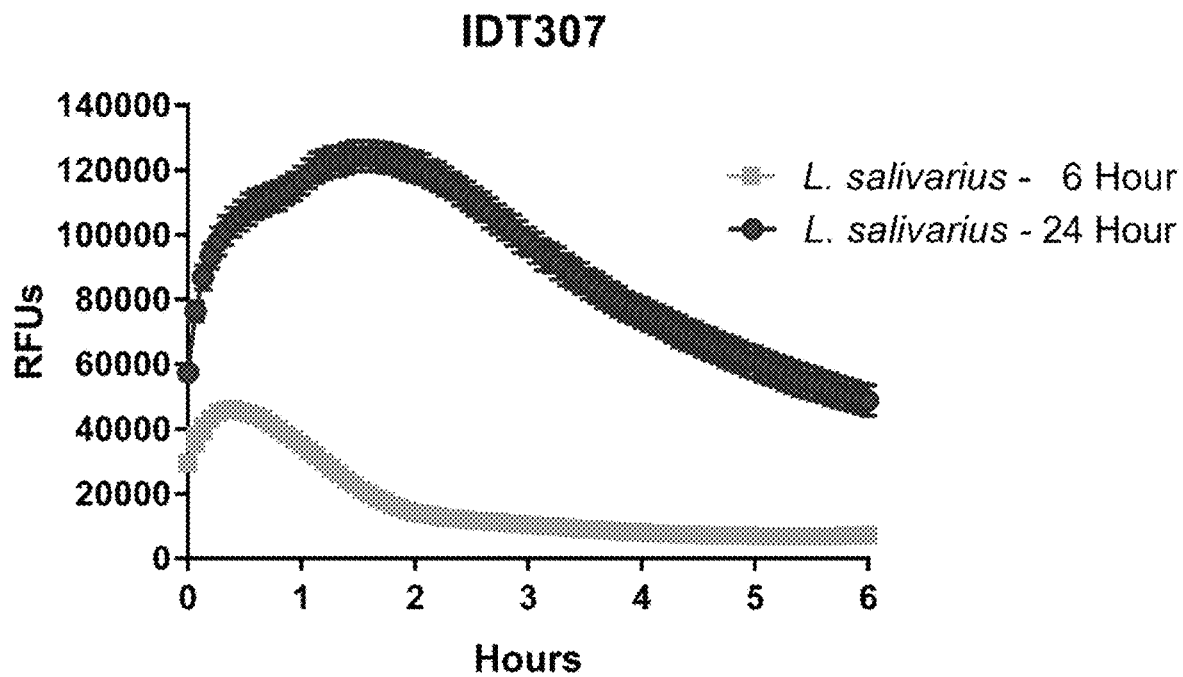
FIG. 5A is a graphical representation of the addition of IDT307 (probe for PMAT-like) after either a 6- or 24-hour incubation in flat clear-bottomed 96-well microplates showing the dependency of *L. salivarius* biofilm growth on fluorophore uptake.
Figure 5B:
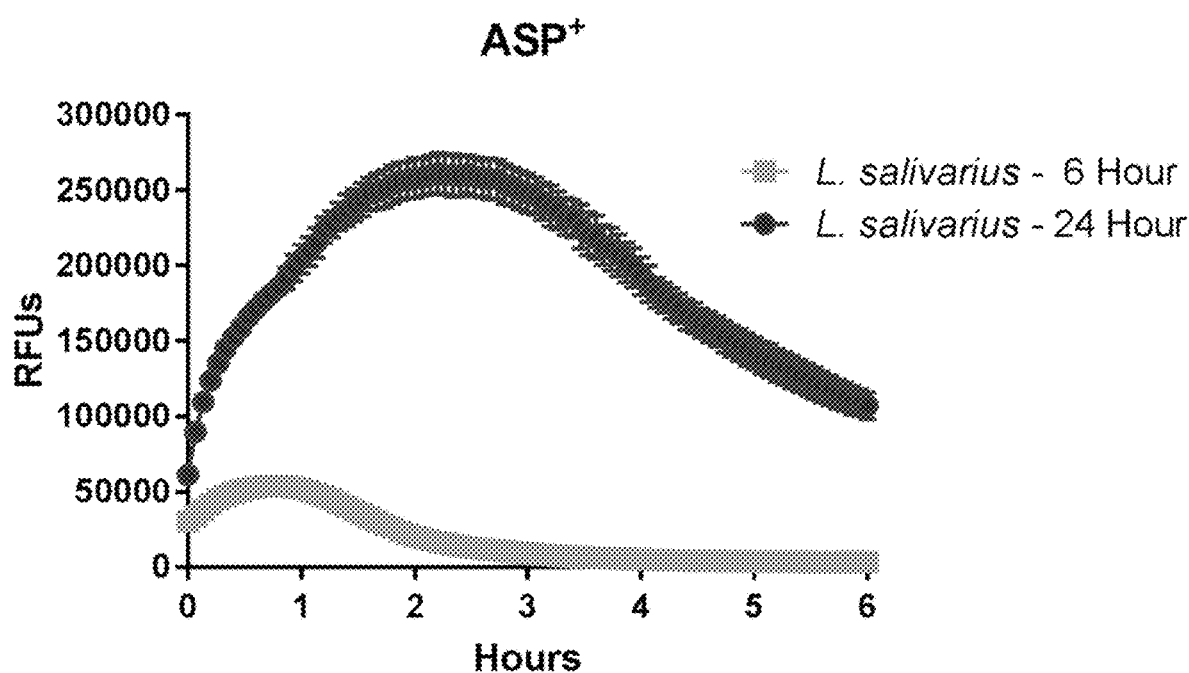
FIG. 5B is a graphical representation of the addition of ASP$^+$ (probe for OCT-like) after either a 6- or 24-hour the incubation in flat clear-bottomed 96-well microplates showing the dependency of *L. salivarius* biofilm growth on fluorophore uptake. Fluorescence (RFU) was immediately measured at 37° C. over six hours as described. Results represent mean±S.E.M of quadruplicate wells and are representative of at least four separate experiments. For some points, the S.E.M. error bars are obscured by the symbol.

In *L. salivarius* biofilms grown over a 6 hour period at 37° C., uptake of the IDT307 and ASP+ fluorescent probes over a succeeding 6 hour interval was rapid and reached maximum fluorescence intensity in <60 min. Intracellular fluorescence decayed rapidly over the next 2-3 hours (FIG. 4A). Similar rapid uptakes of these transporter probes and times to maximum fluorescence were observed in *L. salivarius* biofilms grown for 24 hours (FIG. 5B). However, in comparison to the 6 hour biofilms, fluorescence decay was slower, suggesting that the probes had a longer residence time (>6-hour) in the biofilms established over 24 hours (FIG. 5B). This phenomenon seemed to be selective for *L. salivarius* biofilms, as *L. rhamnosus* biofilms grown under the same conditions failed to take up either transporter probe (FIGS. 4A and 4B). The uptake and decay of these fluorescent probes in both early (6-hour incubation) and established (24-hour incubation) *L. salivarius* biofilms were dependent upon ambient temperature as evidenced by slower increases in IDT307- and ASP+-associated fluorescence and extended time courses of fluorescence quenching in biofilms maintained at 25° C. (FIGS. 4C and 4D).

Figure 6A:
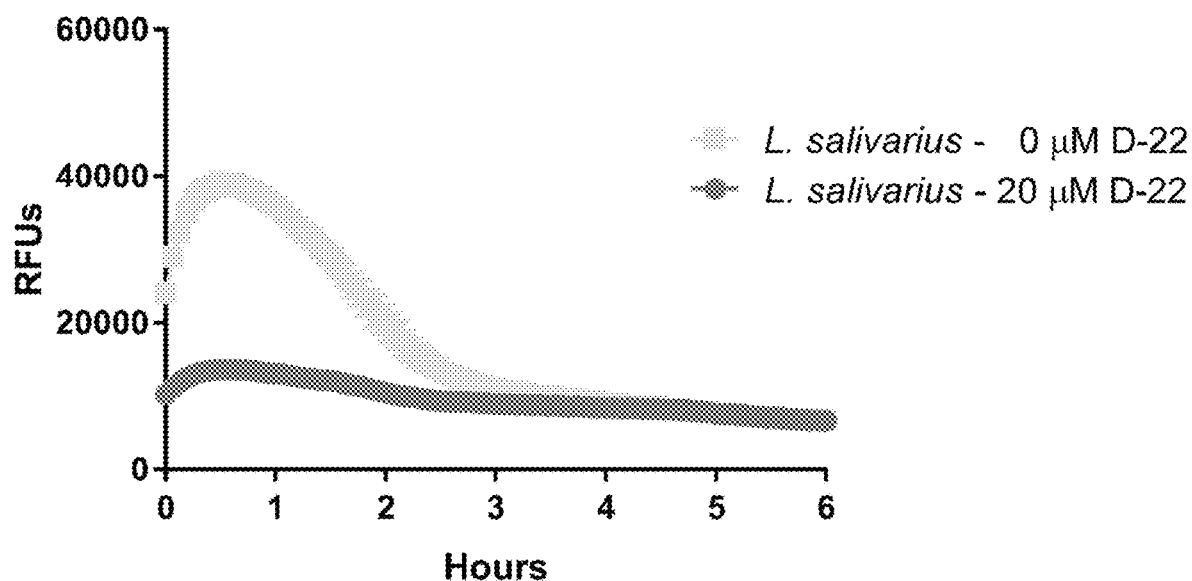
FIG. 6A shows a graphical representation of the effects of decynium-22 on fluorophore uptake into *L. salivarius* biofilms. *L. salivarius* biofilms were allowed to form in flat clear-bottomed 96 well microplates were prepared as described in Example 4. Following a 6 hours incubation of *L. salivarius* culture to form an early biofilm, the medium in each well was gently removed and 100 µl of a pre-warmed solution containing decynium-22 (D-22) was added to achieve a final media concentration of 20 µM (control wells contained the same solvent percentage as did the D-22 wells, see Example 4). The plate was then immediately placed back into a 37° C. incubator for 30 minutes after which time it was removed and 100 µl of a pre-warmed IDT306 was added.
Figure 6B:
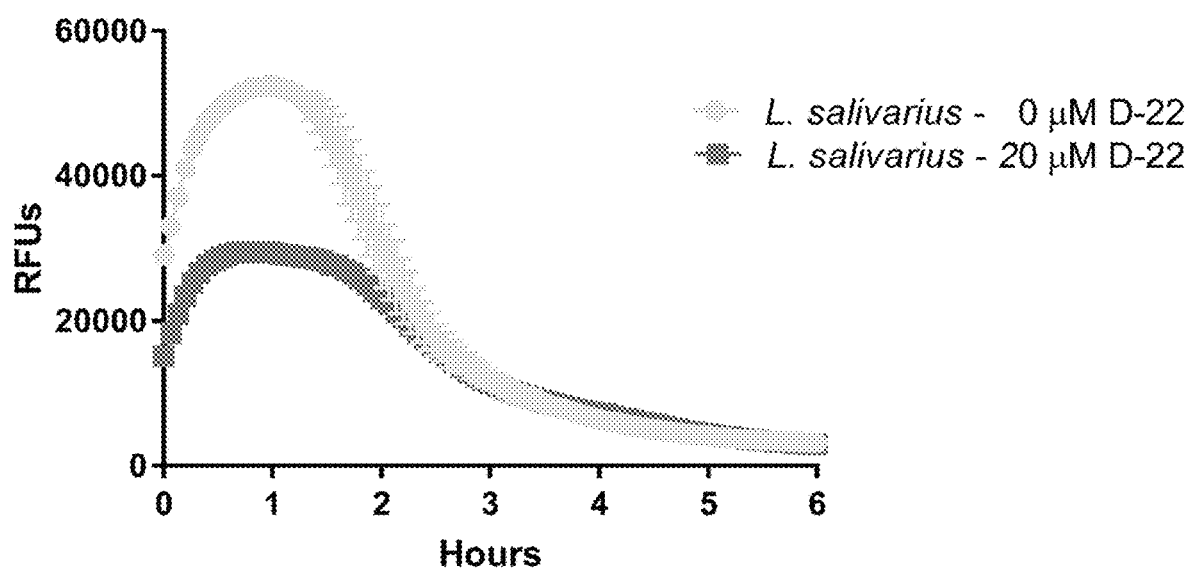
FIG. 6B is a graphical representation of the effects of decynium-22 on fluorophore uptake into *L. salivarius* biofilms as per FIG. 6A except with the addition of ASP$^+$ in place of IDT306. The plate was then immediately placed into the fluorescence reader and measured at 37° C. Results represent mean±S.E.M of triplicate wells and are representative of at least two separate experiments. For some points, the S.E.M. error bars are obscured by the symbol.

Decynium-22 is a potent, competitive substrate for low affinity, high capacity cation transporters, including PMAT and OCTs. Peak increases in IDT307 and ASP+ uptake were blunted in early *L. salivarius* biofilms exposed to decynium-22 at a concentration of 20 µM (FIGS. 6A and 6B). At this concentration, decynium-22 was previously reported to block serotonin uptake through recombinant PMAT or OCTs expressed in HEK293 embryonic kidney cells.

Natural substrates for these transporters, including NE and serotonin, at a concentration of 100 µM markedly inhibited the uptake of IDT307-associated fluorescence into 6 hour *L. salivarius* biofilms (FIG. 7). At an identical concentration, sodium nitrite also inhibited the rapid rise in IDT307-associated fluorescence (FIG. 7). Among its many effects, nitrite ion inhibits active transport processes in aerobic and facultative anaerobic bacteria.

DISCUSSION

This example further shows the existence of bacterial PMAT- and OCT-like capabilities that take up fluorescent probes previously characterized on mammalian PMAT and OCTs. Fluorophore uptake was shown to be bacterial strain-dependent as it was detected in *L. salivarius*, but not *L. rhamnosus* biofilms. The uptake of IDT307 and ASP+, fluorescent markers of PMAT and OCT-mediated transport respectively, was rapid, but less sustained in thinner (6 hour) biofilms than in thicker (24 hour) biofilms. The results imply the ability of the host to interact with microorganisms through direct microbial-neurochemical interactions when excess host-generated biogenic amines may be secreted into the intestinal lumen, such as during periods of stress. Bacterial analogs of mammalian biogenic amine transporters may contribute to the ability of the microbiota-gut-brain axis to influence brain function and ultimately behavior. Further, administration of a probiotic with these biogenic amine-transporting functions to a subject would help to reduce high levels of free biogenic amines in the gut.

A preliminary characterization of the organic cation transport capability, by examining the dependence of fluorophore uptake on ambient temperature and nitrite-sensitive active transport in *L. salivarius* biofilms, showed that the initial rise in intracellular fluorescence and the rate of fluorescence decay were slower at 25° C. than at 37° C. However, peak fluorescence did not appear to be temperature-sensitive, suggesting that temperature affected uptake kinetics but not intracellular capacity to contain the fluorophore. In addition to its temperature sensitivity, uptake of the PMAT probe was abolished in biofilms pretreated with the metabolic inhibitor, sodium nitrite. These findings indicate that screening may be done over a wide range of temperatures and time points.

Mammalian PMAT and OCTs are sensitive to the selective cation transport inhibitor decynium-22. This inhibitor was found to attenuate peak IDT307 or ASP+-associated fluorescence in *L. salivarius* biofilms, showing that a PMAT- and OCT-like capability exists in strains of these bacteria. Moreover, the biogenic amines NE and serotonin similarly attenuated IDT307-associated uptake and peak fluorescence intensity in the biofilms. This demonstration of competitive substrate inhibition further characterizes the screening using host-related substrates.

Example 5: Inhibition of PMAT- and OCT-Like Uptake

To further validate the presence of PMAT- and OCT-like capabilities with an additional inhibitor, fluoxetine was tested against strains of *Lactobacillus*.

To assess inhibition of PMAT- and OCT-like capabilities in *L. salivarius*, fluoxetine, a selective serotonin reuptake inhibitor, was introduced at different concentrations in combination with either the IDT307 or ASP+ fluoroprobe. Plates were prepared as above in Example 4 and following 6 hours (FIGS. 8A and B for PMAT and OCT respectively) or 24 hours (FIGS. 8C and D for PMAT and OCT respectively) of incubation the media was gently removed and replaced with 100 µl of pre-warmed IMDM media with or without different concentrations of fluoxetine. The concentrations of fluoxetine were 0.3125 mM, 0.625 mM, 1.25 mM, or 2.5 mM. The plate was then incubated at 37° C. for 30 minutes. Following incubation, 100 µl of pre-warmed fluorophore was added to the appropriate wells. The plate was then immediate placed into the fluorescence reader and measured at 37° C. As shown in FIG. 8A-D, fluoxetine showed a concentration-dependent inhibition at concentrations below 0.625 mM, and total inhibition at higher concentrations in both early and late biofilms.

These results show that fluoxetine is an effective inhibitor of *Lactobacillus* PMAT- and OCT-like uptake functions.

Example 6: In Vivo Administration of Fluoxetine

Fluoxetine was administered on a daily basis by the oral route to male mice for 28 days in order to determine if any modulation in microbial communities could be obtained.

To classify the microbial communities, the genomes of isolated bacteria were sequenced and compared. Genomic DNA isolation was obtained using the PowerSoil DNA Isolation Kit (MoBio, Carlsbad, CA) on cecal and fecal samples. Assays were performed in accordance with the manufacturer's protocol with the following modifications: samples were incubated at 70° C. for 10 minutes immediately after addition of the C1 solution and the initial vortex step was extended to 20 minutes to thoroughly homogenize the samples. The purified bacterial genomic DNA extracts were quantified using a Qubit 2.0 Fluorometer (Life Technologies, Carlsbad, CA), and stored at −20° C. in 10 mM Tris buffer. For Illumina sequencing, bacterial genomic DNA was amplified using the Earth Microbiome Project barcoded primer set, adapted for the Illumina HiSeq2000 and MiSeq by adding nine extra bases in the adapter region of the forward amplification primer that support paired-end sequencing. The V4 region of the 16S rRNA gene (Illumina, 515F-806R) was amplified with region-specific primers that included the Illumina flowcell adapter sequences. The reverse amplification primer also contained a twelve base barcode sequence that supported pooling of up to 2,167 different samples in each lane. Each 25 µl PCR reaction contained 12 l of MoBio PCR Water (Certified DNA-Free), 10 µl of 5 Prime HotMasterMix (1×), 1 µl of Forward Primer (5 M concentration, 200 µM final), 1 µl Golay Barcode Tagged Reverse Primer (5 µM concentration, 200 µM final), and 1 of template DNA. The conditions for PCR were as follows: 94° C. for 3 minutes to denature the DNA, with 35 cycles at 94° C. for 45 s, 50° C. for 60 s, and 72° C. for 90 s; with a final extension of 10 min at 72° C. to ensure complete amplification. The PCR amplicons were quantified using PicoGreen (Invitrogen) and a plate reader. Once quantified, different volumes of each of the products were pooled into a single tube so that each amplicon was represented equally. This pool was then cleaned up using Ultra-Clean® PCR Clean-Up Kit (MoBIO), and quantified using the Qubit (Invitrogen). After quantification, the molarity of the pool was determined and diluted down to 2 nM, denatured, and then diluted to a final concentration of 6.75 µM with a 10% PhiX spike for sequencing on the Illumina MiSeq.

In total, 60 fecal samples, representing 20 samples for each time point (day 0, 15, and 28) with 10 samples for the control and treatment groups, respectively, were used for 16S rRNA gene amplicon sequencing using Illumina MiSeq with 151 bp paired-end sequencing technology. 16S rRNA gene PCR and library preparation and sequencing were completed at the Environmental Sample Preparation and Sequencing Facility at Argonne National Laboratory. Sequence analysis was performed using mothur version 1.39.3 following the mothur MiSeq SOP available at the mothur website. Briefly, contigs were joined with "make.contigs", reads longer than 250 bp, harboring any ambiguous bases or with more than 8 consecutive homopolymers were excluded using "screen.seqs". Reads were aligned to the SILVA NR128 reference database. Chimeric sequences were removed with "chimera.uchime" and the remaining reads were clustered into operational taxonomic units (OTUs) using a 97% similarity threshold and taxonomy was assigned to OTUs using the SILVA NR 128 reference database. Analyses of statistically significant differences on OTU, genus, and phylum level were done with the LEfSe implementation in mothur; for this, p-values <0.05 were considered statistically significant. For determination of differences between groups on community level, analysis of molecular variance (AMOVA) and analysis of similarity (ANOSIM) implemented in mothur were used. Heatmaps were generated with JColorGrid. For better taxonomic classification, the OTUs were searched against the 16S rRNA gene sequences of the Mouse Intestinal Bacterial Collection isolates (miBC) using BlastN.

In total, 1.42 million reads (from 60 samples) were obtained after merging of the forward and reverse reads. The sequencing data has been submitted to the NCBI Sequence Read Archive SRA. After quality control, 1.134 million high quality reads remained for the analyses. These reads were clustered into 1,612 OTUs with at least 10 reads per OTU. On phylum level, the microbiota of the mice in this experiment was dominated by Firmicutes (51.4%), Bacteroidetes (44.8%), Tenericutes (1.2%), and Deferibacteres (1.2%). The other phyla showed less than 1% relative abundance among the samples. Firmicutes trended (p=0.08) to be more abundant than Bacteroidetes in the fluoxetine-treated mice.

Figure 9:
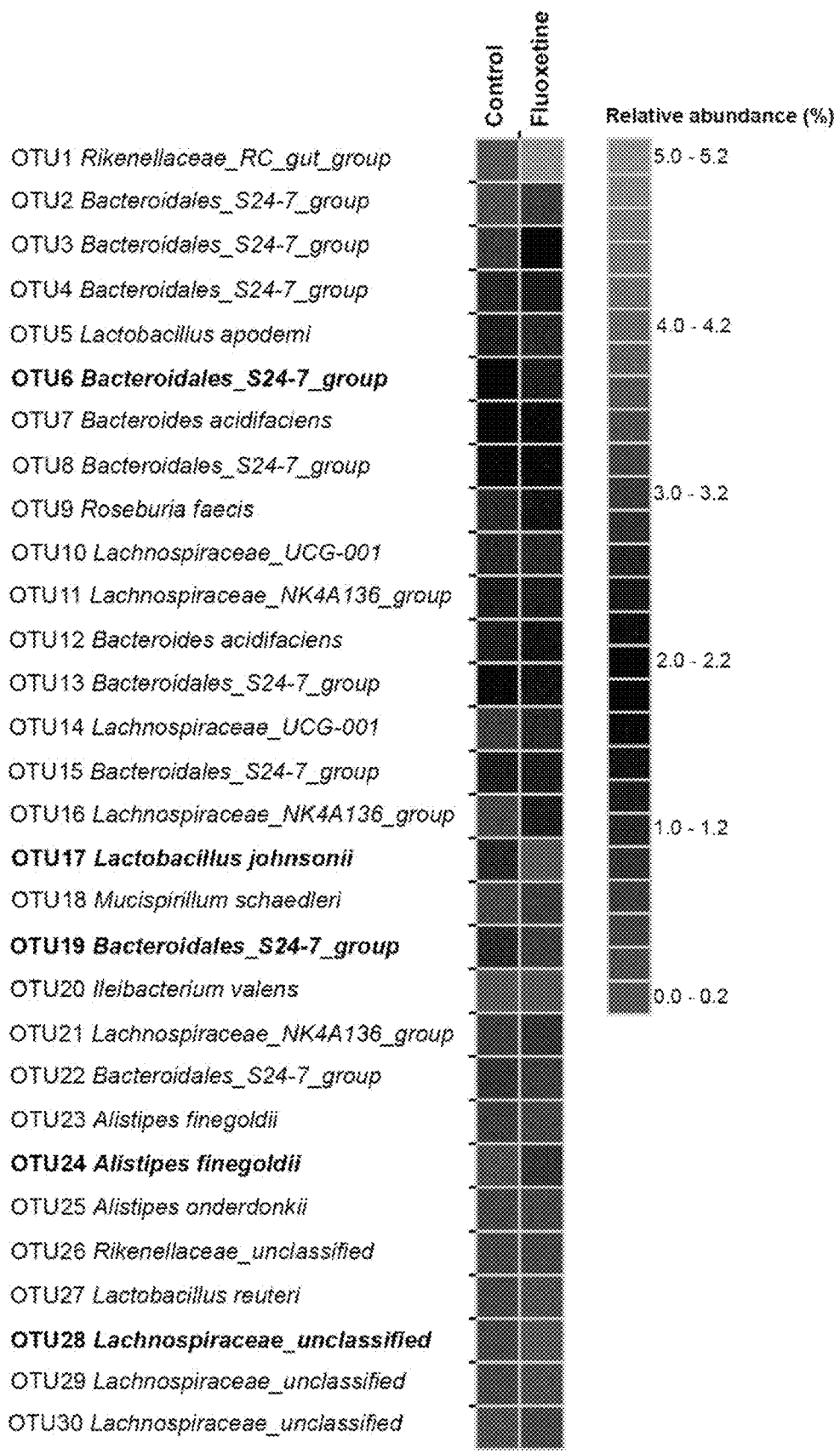
FIG. 9 shows the relative abundance of the 30 most abundant OTUs. The heatmap shows median relative abundance values for OTUs in the control group and Fluoxetine-treated mice. OTUs which were statistically significantly different between the two groups are highlighted in bold.

The calculated species richness and diversity indicators were inconsistent within the groups. Some animals showed an increase in species richness and diversity during the trial, and others remained similar or decreased. No statistical significant differences were found in the richness and diversity estimators between the control and the fluoxetine treated group. Most of the OTUs had highest similarity to phylotypes described as members of the murine gastrointestinal tract (FIG. 9). The results revealed clear differences in abundance of OTUs between the two groups. Among the OTUs, 121 OTUs were different between control and the fluoxetine group; 21 of these OTUs were among the 100 most abundant OTUs. These OTUs comprised several OTUs affiliating to the Bacteroidales S24-7 group, *Lachnospiraceae, Roseburia, Alistipes* and one *Lactobacillus* OTU. The Bacteroidales S24-7 groups, some *Lachnospiraceae* OTUs and the *Lactobacillus* OTU17 (the latter showed a 7.4 fold decrease under fluoxetine treatment) were more abundant in the control group, whereas the *Alistipes* OTU24, the *Lachnoclostridium* OTU and *Anaerotruncus* OTUs were more abundant in the fluoxetine-treated mice (FIG. 9).

Figure 10:
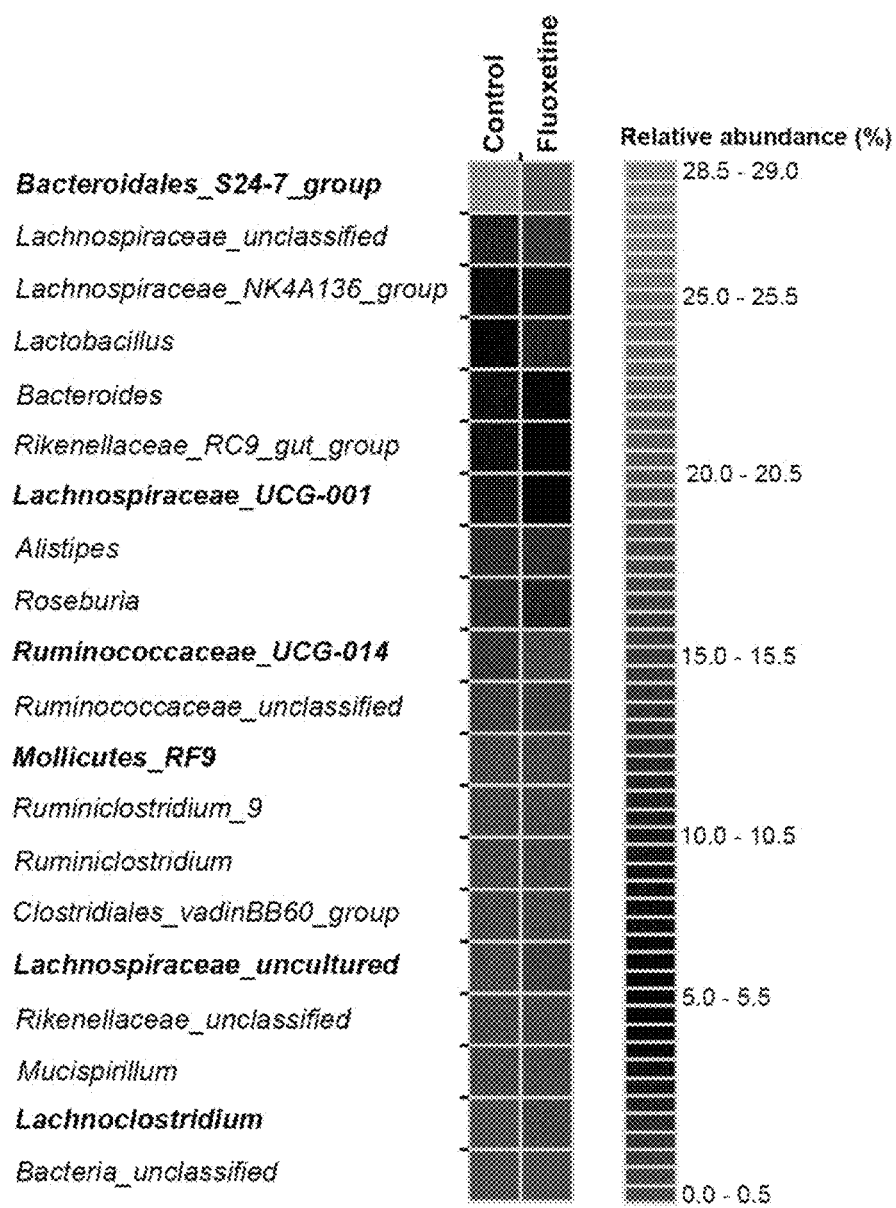
FIG. 10 shows the relative abundance of the 20 most abundant genera. The heatmap shows median relative abundance values for genera in the control group and Fluoxetine-treated mice. Genera which were statistically significantly different between the two groups are highlighted in bold.

On the genus level, Bacteroidales S24-7 group, unclassified *Lachnospiraceae*, and *Lachnospiraceae*_NK4A136 group were most abundant (FIG. 10). Similar to the findings on OTU level, also on genus level, a genus belonging to the Bacteroidales S24-7 group and genera affiliating to the *Ruminococcaceae*_UCG-014 and to the Mollicutes_RF9 group were more abundant in the control group. Genera affiliating to the *Lachnospiraceae*_UCG-001, *Lachnospiraceae*_UCG-006 and to uncultured *Lachnospiraceae* showed higher abundance in the fluoxetine treated mice. In addition, *Anaerotruncus, Ruminiclostridium*_5, unclassified *Coriobacteriaceae*, and *Lachnoclostridium* were more abundant in the fluoxetine treated mice.

Comparisons on whole community level using AMOVA and ANOSIM revealed statistically significant differences between the microbial communities of the control group and the fluoxetine-treated mice (p=0.02 and p=0.05, respectively).

Overall, the data revealed differences between the microbial communities of mice from the control group compared to the fluoxetine treated mice indicative of a shift of microbial communities towards dysbiosis induced by the fluoxetine treatment. While some OTUs were more abundant in the control group, such as several Bacteroidales S24-7 OTUs, one *Lactobacillus* OTU and some OTUs affiliating to the *Lachnospiraceae*, a number of OTUs and genera were more abundant in the treatment group, including *Alistipes*, various *Lachnospiraceae* OTUs, *Lachnoclostridium* and *Anaerotruncus*.

Many of the OTUs which were higher in the fluoxetine treated mice are associated with dysbiosis and additional illness or non-physiological conditions, while some of the OTUs higher in the control group have been associated with beneficial properties. The OTUs which were higher in the fluoxetine-treated mice that have been associated with other illnesses and various indicators of dysbiosis included *Alistipes* OTU24, *Anaerotruncus, Lachnospiraceae* OTUs 32, 38, 86, and 93, *Roseburia* OTUs 45, 69, and 74, and *Lachnoslostridium* OTU46. Additionally, the Bacteroidales S24-7 group, which was lower in the fluoxetine-treated mice, has been associated with beneficial roles in gut health and possibly with normal brain development. Similarly, *Lactobacillus* was also lower in the fluoxetine-treated mice. Taken together, administration of fluoxetine may cause ailments in subjects. Thus, it would be beneficial to provide subjects with a probiotic with biogenic amines and related substrates or their precursors, such as with fluoxetine, in order to avoid the dysbiotic effects of administering fluoxetine alone.

Further these data demonstrate that microbiota belonging to a specific genus, such as *Lactobacillus*, and which have been shown to possess PMAT- and OCT-like capabilities, can have their abundance influenced by an SSRI. The ability of fluoxetine to influence the abundance of the other genera indicates that they also possess biogenic amine capabilities similar to that of Lactobacilli.

Additionally, these data indicate that a microbial endocrinology-based mechanism involving PMAT- and OCT-like biogenic amine uptake capabilities, is one of the mechanisms responsible. The observed differential changes in the abundance of specific microbiota genera that are well correlated (as has been discussed above) with gut dysbiosis, indicate that the well-recognized negative side effects of fluoxetine may be due to changes in the gut microbial community, which stem from disruptions in bacterial biogenic amine uptake mechanisms. The results of this study further suggest that restoration of normal microbial diversity, through the co-administration of a probiotic with fluoxetine or other drug or by administering a SSRI, a selective serotonin-norepinephrine reuptake inhibitor (SSNRI) or other drug which is not sequestered by gut microbes to achieve a target uptake capability profile, may have therapeutic potential to ameliorate some of the negative side effects of fluoxetine, other drugs, or a high level of biogenic amines, thereby increasing drug efficacy and patient compliance.

Example 7: Influence of Duloxetine and Amitriptyline on Biogenic Amine Transport Two other antidepressant drugs that are chemically unrelated to fluoxetine, duloxetine and amitriptyline, were tested for their action on PMAT- and OCT-like functionalities in Lactobacilli to determine if they may also be used as inhibitors. Cells were grown in 96-well plates for 24 hours to allow for biofilm formation as above. Similar to the treatments in Example 4 and 6, the cells were then treated with either 1 mg/ml of either duloxetine or amitriptyline for *L. salivarius* or 2 mg/ml for *L. reuteri*. IDT307 or ASP$^+$ was then used to measure the effects of each antidepressant drug on the cells ability to take up the fluorophore.

Figure 11A:
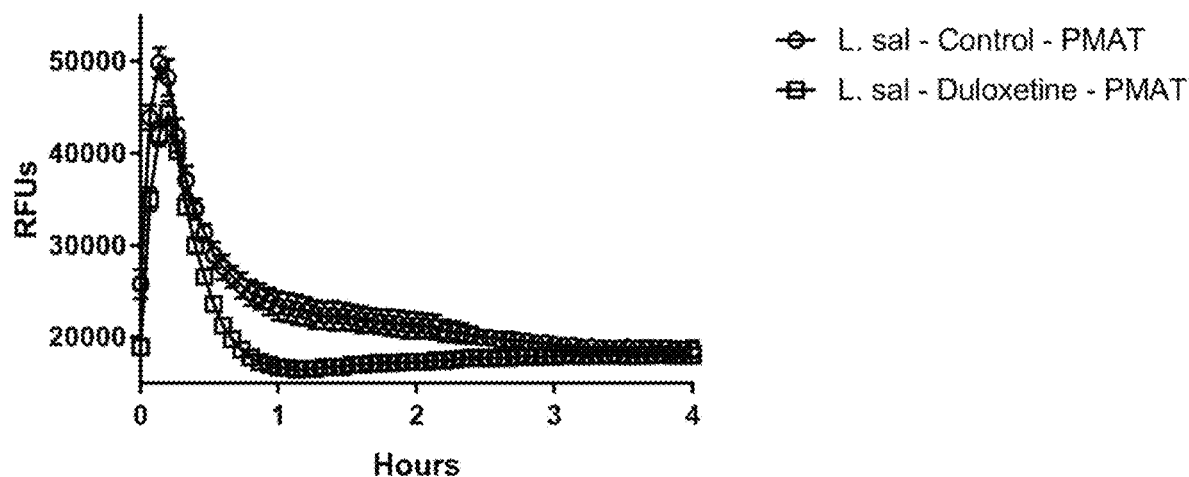
FIG. 11A is a graphical representation of the effect of duloxetine, an antidepressant drug, on PMAT-like transport function in *L. salivarius*.
Figure 11B:
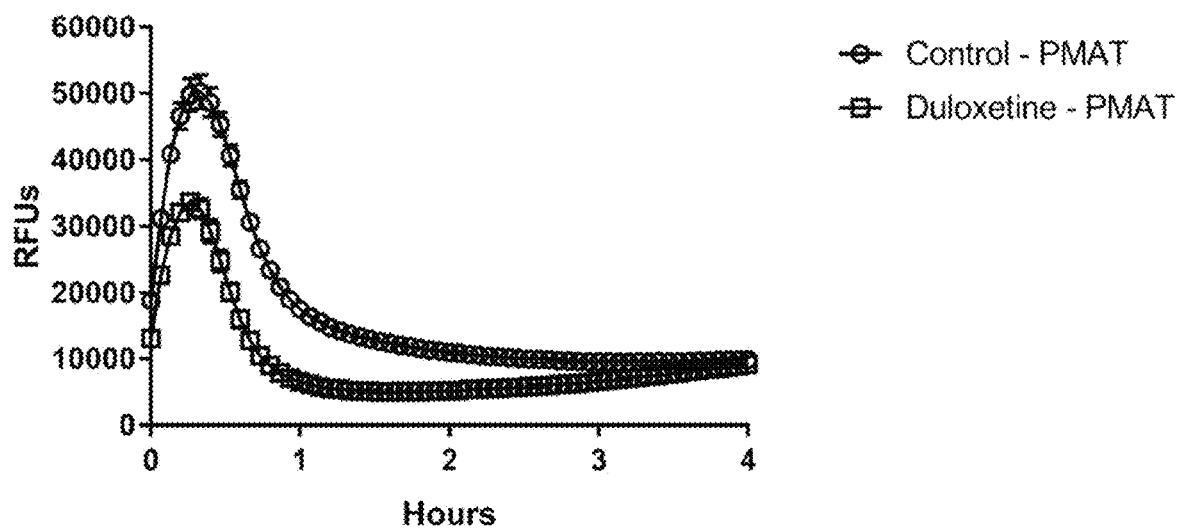
FIG. 11B is a graphical representation of the effect of duloxetine on PMAT-like transport function in *L. reuteri*.
Figure 11C:
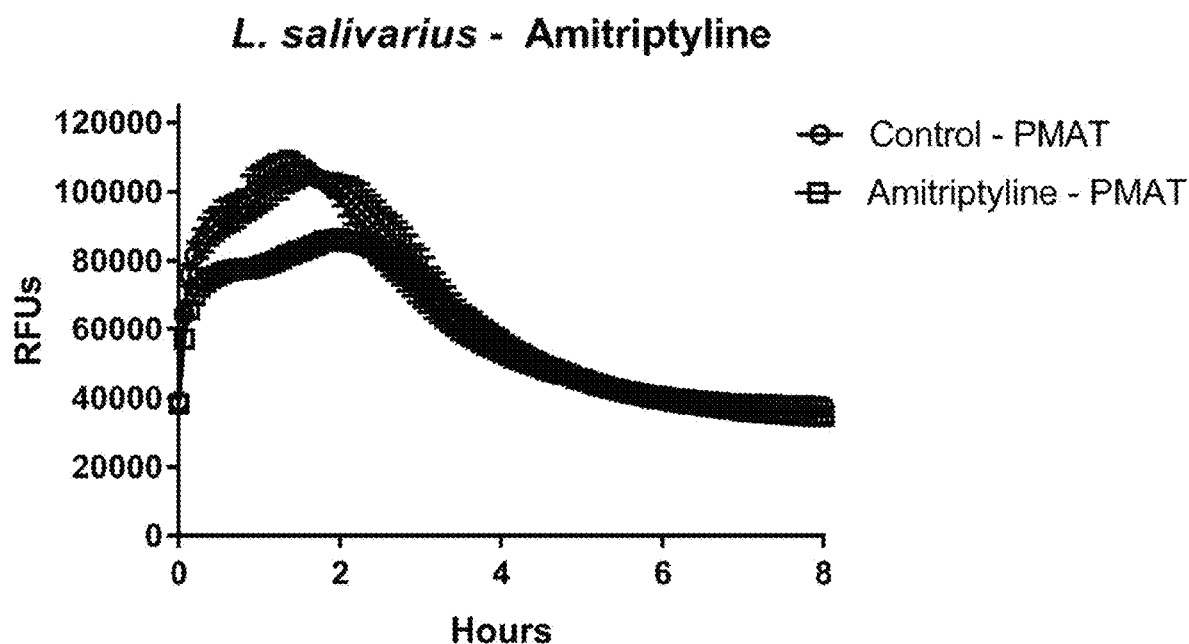
FIG. 11C is a graphical representation of the effect of amitriptyline, an antidepressant drug, on PMAT-like transport function in *L. salivarius*. The cells were treated with either 1 mg/ml of media of either duloxetine (FIG. 11A) or amitriptyline (FIG. 11C) for *L. salivarius* or 2 mg/ml for *L. reuteri* (FIG. 11B). Results represent mean 1 S.E.M. of triplicate wells and are representative of at least two separate experiments. For some points, the S.E.M. error bars are obscured by the symbol.
Figure 12A:
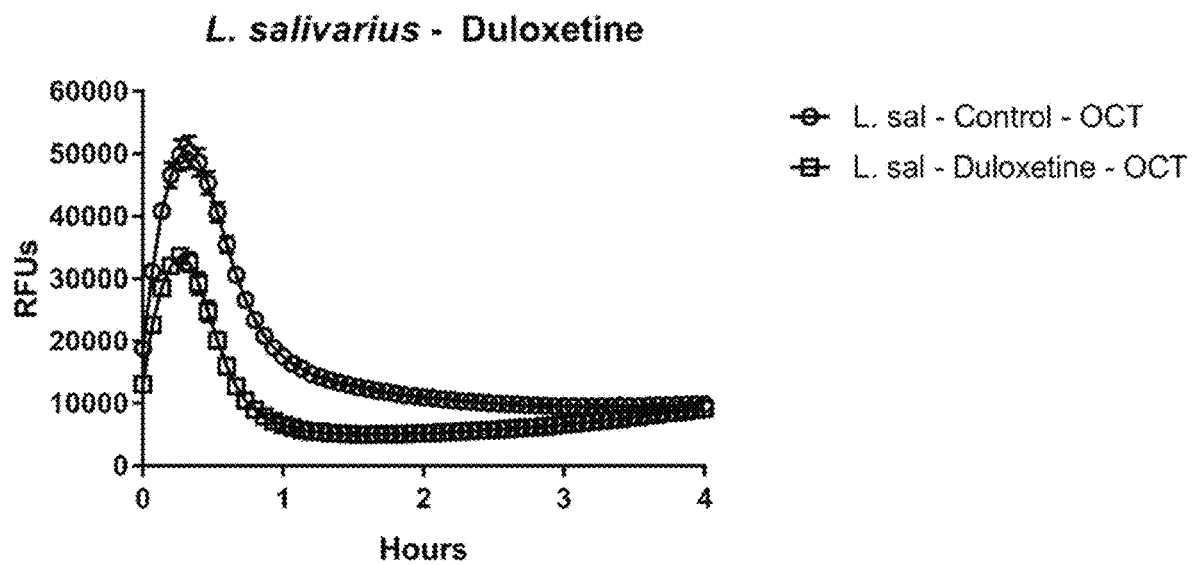
FIG. 12A is a graphical representation of the effect of duloxetine, an antidepressant drug, on OCT-like transport function in *L. salivarius*.
Figure 12B:
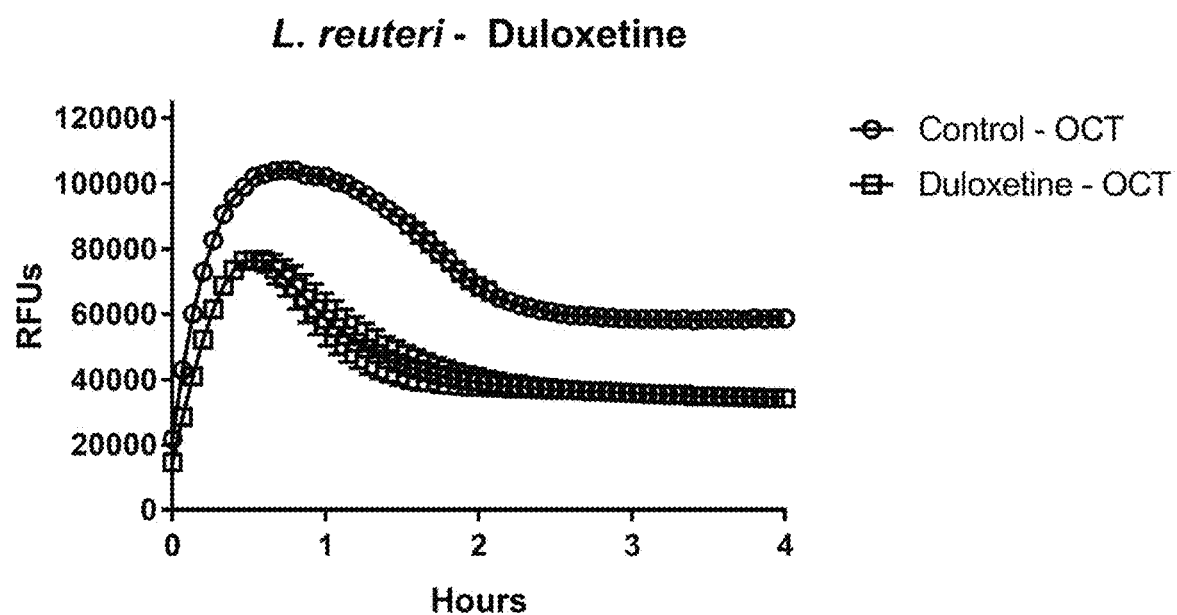
FIG. 12B is a graphical representation of the effect of the effect of duloxetine on OCT-like function in *L. reuteri*.
Figure 12C:
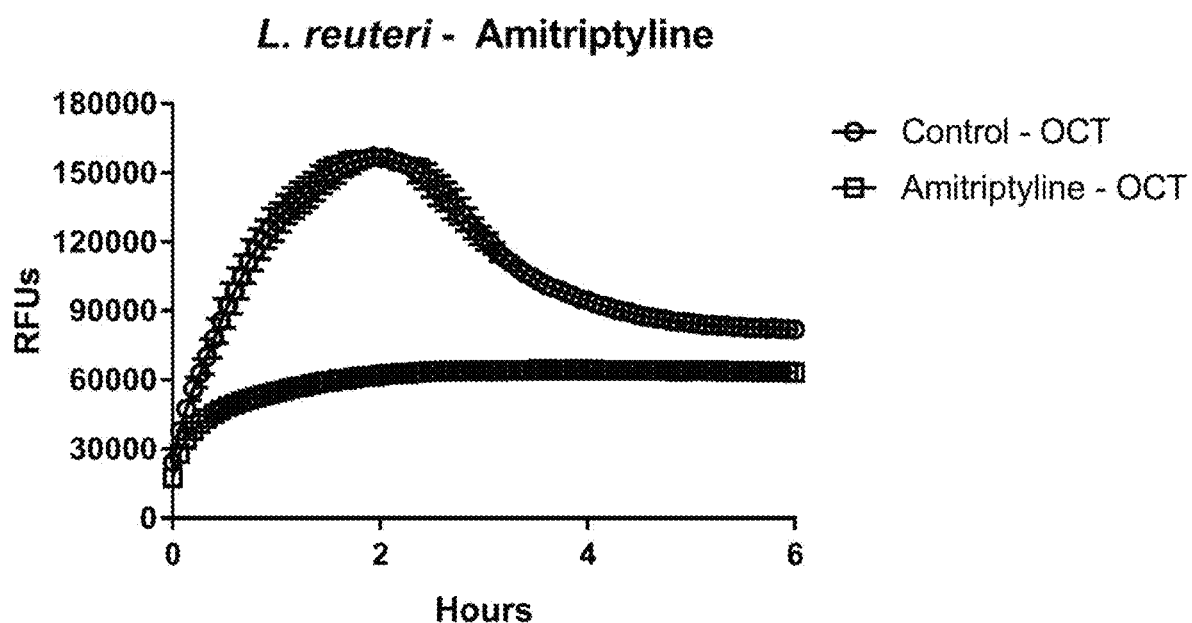
FIG. 12C is a graphical representation of the effect of amitriptyline, an antidepressant drug, on OCT-like transport function in *L. reuteri*. The cells were treated with either 1 mg/ml of media of either duloxetine or amitriptyline for *L. salivarius* (FIG. 12A) or 2 mg/ml for *L. reuteri* (FIGS. 12B and 12C). Results represent mean±S.E.M. of triplicate wells and are representative of at least two separate experiments. For some points, the S.E.M. error bars are obscured by the symbol.

As shown in FIGS. 11-12, both duloxetine and amitriptyline influenced uptake of the fluorophores. For both PMAT- (FIG. 11) and OCT-like (FIG. 12) uptake capabilities, duloxetine produced a larger attenuation of fluorophore uptake in *L. reuteri* (FIGS. 11B and 12B) than in *L. salivarius* (FIGS. 11A and 12A), though both strains showed some attenuation in the uptake of both fluorophores. Amitriptyline produced a much stronger inhibitory effect on fluorophore uptake, as evidenced by the larger attenuation of peak fluorescence measured in the control cells, and in OCT-like capability in *L. reuteri* (FIG. 12C) relative to PMAT-like capability in *L. salivarius* (FIG. 11C).

This Example further validates the screening over a wide range of possible inhibitors.

The inventions being thus described, it will be obvious that the same may be varied in many ways. Such variations are not to be regarded as a departure from the spirit and scope of the inventions and all such modifications are intended to be included within the scope of the following claims.

What is claimed is:

1. A method of modulating a subject's microbiome's capability of taking up biogenic amines, the method comprising:
   obtaining a sample comprising a representative population of a microbiome from a subject,
     wherein said microbiome comprises one or more probiotic strains;
   screening the probiotic strains to detect a probiotic strain capable of taking up biogenic amines, wherein the taking up is done through plasma membrane monoamine transporter-like and/or one or more organic cation transporter-like proteins;
   determining a target uptake capability profile for the subject; and
   administering an effective amount of the probiotic strain capable of taking up a biogenic amine and/or a plasma membrane monoamine transporter-like and/or organic cation transporter-like inhibitor to the subject in need thereof, thereby providing the target uptake capability profile in the subject.

2. The method of claim 1, wherein said administering results in ameliorating adverse effects of biogenic amines and/or changing the concentrations of free biogenic amines in said subject.

3. The method of claim 1, wherein said probiotic strain is at least one of *Candida* spp., *Debaryomyces* spp., *Kluyveromyces* spp., *Saccharomyces* spp., *Yarrowia* spp., *Bifidobacteria* spp., *Lactobacillus* spp., *Candida humilis, Debaryomyces hansenii, Debaryomyces occidentalis, Kluyveromyces lactis, Kluyveromyces lodderae, Kluyveromyces marxianus, Saccharomyces cerevisiae, Yarrowia lipolytica, Bifidobacterium bifidum, Bacillus* spp., *Bacteroides* spp., *Bifidobacterium* spp., *Brevibacteria* spp., *Clostridium* spp., *Enterococcus* spp., *Escherichia coli, Lactococcus* spp., *Staphylococcus* spp., *Bacillus coagulans, Bacillus subtilis, Bacteroides fragilis, Bacteroides subtilis, Bacteroides thetaiotaomicron, Bifidobacterium bifidum, Bifidobacterium infantis, Bifidobacterium lactis, Bifidobacterium longum, Clostridium butyricum, Enterococcus faecium, Alistipes* spp., *Lachnoclostridium* spp., *Anaerotruncus* spp., *Ruminococcaceae* spp., *Ruminiclostridium* spp., *Coriobacteriaceae* spp., and/or *Lachnospiraceae* spp.

4. The method of claim 1, wherein said transporter inhibitor is one or more of cimetidine, decynium-22, dipyridamole, quinidine, quinine, tryptamine, and/or verapamil.

5. The method of claim 1, wherein detecting comprises contacting the probiotic strain with at least one fluorophore and detecting the increase in fluorescence in said probiotic strain.

6. The method of claim 5, wherein said fluorophore is IDT307 and/or ASP$^+$.

7. A method for selecting compounds which probiotic strains are incapable of taking up, comprising:

screening probiotic strains to detect a probiotic strain capable of taking up biogenic amines,
    wherein said taking up is done through plasma membrane monoamine transporter-like and/or one or more organic cation transporter-like proteins;
selecting the probiotic strain which is capable of taking up a biogenic amine;
administering to said probiotic strain a compound;
detecting the uptake of said compound; and
selecting the compound if the probiotic strain is incapable of taking up and/or sequestering intracellularly said compound.

8. The method of claim 7, wherein said probiotic strain is at least one of *Candida* spp., *Debaryomyces* spp., *Kluyveromyces* spp., *Saccharomyces* spp., *Yarrowia* spp., *Bifidobacteria* spp., *Lactobacillus* spp., *Candida humilis*, *Debaryomyces hansenii*, *Debaryomyces occidentalis*, *Kluyveromyces lactis*, *Kluyveromyces lodderae*, *Kluyveromyces marxianus*, *Saccharomyces cerevisiae*, *Yarrowia lipolytica*, *Bifidobacterium bifidum*, *Bacillus* spp., *Bacteroides* spp., *Bifidobacterium* spp., *Brevibacteria* spp., *Clostridium* spp., *Enterococcus* spp., *Escherichia coli*, *Lactococcus* spp., *Staphylococcus* spp., *Bacillus coagulans*, *Bacillus subtilis*, *Bacteroides fragilis*, *Bacteroides subtilis*, *Bacteroides thetaiotaomicron*, *Bifidobacterium bifidum*, *Bifidobacterium infantis*, *Bifidobacterium lactis*, *Bifidobacterium longum*, *Clostridium butyricum*, *Enterococcus faecium*, *Alistipes* spp., *Lachnoclostridium* spp., *Anaerotruncus* spp., *Ruminococcaceae* spp., *Ruminiclostridium* spp., *Coriobacteriaceae* spp., and/or *Lachnospiraceae* spp.

9. The method of claim 7, wherein detecting comprises contacting the probiotic strain with a fluorophore and altering intracellular fluorescence in said probiotic strain.

10. The method of claim 9, wherein said fluorophore is IDT307 and/or ASP$^+$.

* * * * *